US007700277B2

(12) United States Patent
Ambrose et al.

(10) Patent No.: US 7,700,277 B2
(45) Date of Patent: Apr. 20, 2010

(54) USE OF POLYMORPHISMS IN HUMAN OATP-C ASSOCIATED WITH AN EFFECT ON STATIN PHARMACOKINETICS IN HUMANS IN STATIN THERAPY

(75) Inventors: Helen Jean Ambrose, Macclesfield (GB); Ruth March, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 536 days.

(21) Appl. No.: 10/566,054

(22) PCT Filed: Jul. 26, 2004

(86) PCT No.: PCT/GB2004/003236

§ 371 (c)(1),
(2), (4) Date: Jun. 27, 2006

(87) PCT Pub. No.: WO2005/012566

PCT Pub. Date: Feb. 10, 2005

(65) Prior Publication Data

US 2007/0031838 A1 Feb. 8, 2007

(30) Foreign Application Priority Data

Jul. 26, 2003 (GB) ................................. 0317592.4

(51) Int. Cl.
*C12Q 1/68* (2006.01)
*C07H 21/02* (2006.01)
*C07H 21/04* (2006.01)
(52) U.S. Cl. ..................... 435/6; 536/23.1; 435/91.2
(58) Field of Classification Search ....................... None
See application file for complete search history.

(56) References Cited

U.S. PATENT DOCUMENTS

| 4,376,110 | A | 3/1983 | David et al. |
| 4,411,993 | A | 10/1983 | Gillis |
| 4,486,530 | A | 12/1984 | David et al. |
| 4,543,439 | A | 9/1985 | Frackelton, Jr. et al. |
| RE32,011 | E | 10/1985 | Zimmerman et al. |
| 4,902,614 | A | 2/1990 | Wakabayashi et al. |
| 5,210,015 | A | 5/1993 | Gelfand et al. |
| 5,487,972 | A | 1/1996 | Gelfand et al. |
| 2002/0090622 | A1 | 7/2002 | Adeokun et al. |
| 2004/0235006 | A1 | 11/2004 | Adeokun et al. |

FOREIGN PATENT DOCUMENTS

| EP | 0 332 435 | | 4/1992 |
| EP | 1 186 672 | A2 * | 3/2002 |
| EP | 1 186 672 | | 11/2005 |
| GB | 2 228 998 | | 9/1990 |
| WO | WO 95/13399 | | 5/1995 |
| WO | WO 00/08157 | | 2/2000 |

OTHER PUBLICATIONS

Lee, E. et al., Clin. Pharmacol. Ther., vol. 78, pp. 330-341 (2005).*
Bottorff, M., Atherosclerosis, vol. 147, Suppl. 1, pp. S23-S30 (1999).*
Hamelin, B.A. et al., Trends in Pharm. Sci., vol. 19, pp. 26-37 (1998).*
EMBL Accession No. AB026257 dated Jul. 29, 2000.
EMBL Accession No. AC022335 dated Oct. 31, 2002.
EMBL Accession No. AF205071 dated Dec. 28, 1999.
EMBL Accession No. AJ132573 dated Oct. 7, 2008.
EMBL Accession No. AF060500 dated Jun. 15, 1999.
Alting-Mees et al., "Monoclonal Antibody Expression Libraries: A Rapid Alternative to Hybridomas," *Strategies in Molecular Biology*, 1990, 3:1-9.
Brown, "Rosuvastatin is a High Affinity Substrate of Hepatic Organic Anion Transporter OATP-C," *Atherosclerosis Supplements 2*, 2001, p. 90, Abstract P174.
Chong and Seeger, "Atorvastatin calcium: an addition to HMG-CoA reductase inhibitors," *Pharmacotherapy*, 1997, 17(6):1157-1177.
Dujovne, "New lipid lowering drugs and new effects of old drugs," *Current Opinion in Lipidology*, 1997, 8:362-368.
Forbes (ed.), "HMG-CoA reductase inhibitors: a first-line option," *Drugs and Therapy Perspectives*, 1997, 9:1-6.
Gibbs et al., "Detection of Single DNA Base Differences by Competitive Oligonucleotide Priming," *Nucl. Acids Res.*, 1989, 17(7):2437-2448.
Hsiang et al., "A novel human hepatic organic anion transporting polypeptide (OATP2). Identification of a liver-specific human organic anion transporting polypeptide and identification of rat and human hydroxymethylglutaryl-CoA reductase inhibitor transporters," *J. Biol. Chem.*, 1999, 274(52):37161-37168.
Jahng, "Design of a new class of HMG-CoA reductase inhibitors," *Drugs of the Future*, 1995, 20:387-404.
Kathawala, "HMG-CoA reductase inhibitors: an exciting development in the treatment of hyperlipoproteinemia," *Med. Res. Rev.*, 1991, 11:121-146.
Kellick et al., "Focus on atorvastatin: An HMG-CoA reductase inhibitor for Tx of hypercholesterolemia," *Formulary*, 1997, 32:352.
König et al., "Localization and genomic organization of a new hepatocellular organic anion transporting polypeptide," *J. Biol. Chem.*, 2000, 275(30):23161-23168.
Larrick et al., "Polymerase Chain Reaction Using Mixed Primers: Cloning of Human Monoclonal Antibody Variable Region Genes From Single Hybridoma Cells," *Biotechnology*, 1989, 7:934-938.
Nollau and Wagener, "Methods for detection of point mutations: performance and quality assessment," *Clin. Chem.*, 1997, 43:1114-1128.

(Continued)

*Primary Examiner*—Teresa E Strzelecka
(74) *Attorney, Agent, or Firm*—Fish & Richardson P.C.

(57) ABSTRACT

This invention relates to use of polymorphisms in human OATP-C in statin therapy because they are associated with an effect on statin pharmacokinetics (PK) in humans, especially rosuvastatin pharmacokinetics. The invention also relates to the use of OATP-C polymorphisms in predicting the efficacy and safety of statins, whose uptake in to the liver is mediated by OATP-C, especially rosuvastatin.

16 Claims, 3 Drawing Sheets

OTHER PUBLICATIONS

Olsson, "Statin Therapy and Reductions in Low-Density Lipoprotein Cholesterol: Initial Clinical Data on the Potent New Statin Rosuvastatin," *Am. J. Cardiol.*, 2001, 87(suppl):33B-36B.

Park et al., "Pharmacokinetics of pravastatin in heart-transplant patients taking cyclosporine A," *Int. J. Clin. Pharmacol Ther.*, 2002, 40:439-450.

Rowland and Tozer (eds.), "Disease," *Clinical Pharmacokinetics*, 1995, 3rd edition, Chapter 16, pp. 248-266, Williams & Wilkins.

Scatchard, "The Attractions of Proteins for Small Molecules and Ions," *Ann. N.Y. Acad. Sci.*, 1949, 51:660-672.

Stephens et al., "A New Statistical Method for Haplotype Reconstruction from Population Data," *Am. J. Human Genet.*, 2001, 68:978-989.

Tyagi and Kramer, "Molecular Beacons: Probes that Fluoresce Upon Hybridization," *Nat. Biotechnol.*, 1996, 14:303-308.

Watanabe et al., "Synthesis and Biological Activity of Methanesulfonamide Pyrimidine- and N-Methanesulfonyl Pyrrole-Substituted 3,5-Dihydroxy-6-heptenoates, a Novel Series of HMG-CoA Reductase Inhibitors," *Bioorg. Med. Chem.*, 1997, 5:437-444.

Akey et al., "Haplotypes vs single marker linkage disequilibrium tests: what do we gain?", *European Journal of Human Genetics* 9:291-300 (2001).

Anonymous: "OATP-C: SLC01B1" Genecards, Oct. 18, 2005; Retrieved from the Internet: URL:http://www.genecards.org/cgi-bin/carddisp?SLC01B1&search=oatp-c&suff=txt.

Anonymous: "GeneCard for protein-coding SLCO1B1" Genecards, 'Online! XP002317182 Retrieved from the Internet: URL:http://genecards.weizmann.ac.il/cgi-bin/cards/carddisp?SLC01B1&search=oatp-c&suff=txt (Document not attached), retrieved Jan. 25, 2006.

Anonymous: "SNP linked to Gene (geneID: 10599)" Single Nucleotide Polymorphism, 'Online! XP002320267 retrieved from the internet: URL:http://www.ncbi.nlm.nih.gov/SNP//snp_ref.cgi?locusId=10599>, retrieved Jan. 25, 2006.

Calafell et al., "Haplotype Evolution and Linkage Disequilibrium: A Simulation Study", *Hum Hered* 51:85-96 (2001).

Database EMBL 'Online! Mar. 15, 2000, "Homo sapiens chromosome 11 clone RP11-484D2, Working Draft Sequence, 22 unordered pieces." XP002317183 retrieved from EBI accession No. EM_PRO:AC025552 Database accession No. AC025552.

Igel et al., "Pharmacology of 3-Hydroxy-3-Methylglutaryl-Coenzyme A Reductase Inhibitors (Statins), Including Rosuvastatin and Pitavastatin", *J Clin Pharmacology* 42:835-845 (2002).

Jorde, "Linkage Disequilibrium and the Search for Complex Disease Genes", *Genome Research* 10:1435-1444 (2000).

Jung et al., "Characterization of the Human OATP-C (SLC21A6) Gene Promoter and Regulation of Liver-specific OATP Genes by Hepatocyte Nuclear Factor 1α", *J. Biol. Chem.* 276(40):37206-37214 (2001).

Kim, "3-Hydroxy-3-methylglutaryl-coenzyme A reductase inhibitors (statins) and genetic variability (single nucleotide polymorphisms) in a hepatic drug uptake transporter: What's it all about?", *Clinical Pharmacology & Therapeutics* 75(5):381-385 (2004).

König et al., "A novel human organic anion transporting polypeptide localized to the basolateral hepatocyte membrane", *Am. J. Physiol. Gastrointest. Liver Physiol.* 278:G156-G164 (2000).

Kruglyak, "Prospects for whole-genome linkage disequilibrium mapping of common disease genes", *Nature Genetics* 22:139-144 (1999).

Mwinyi et al., "Evidence for inverse effects of *OATP-C (SLC21A6)* *5 and *1b haplotypes on pravastatin kinetics", *Clinical Pharmacology & Therapeutics* 75(5):415-421 (2004).

Niemi et al., "High plasma pravastatin concentrations are associated with single nucleotide polymorphisms and haplotypes of organic anion transporting polypeptide-C (*OATP-C, SLCO1B1*)", *Pharmacogenetics* 14:429-440 (2004).

Nishizato et al., "Polymorphisms of *OATP-C (SLC21A6)* and *OAT3 (SLC22A8)* genes: Consequences for pravastatin pharmacokinetics", *Clinical Pharmacology & Therapeutics* 73(6):554-565 (2003).

Nozawa et al., "Genetic Polymorphisms of Human Organic Anion Transporters OATP-C (SLC21A6) and OATP-B (SLC21A9): Allele Frequencies in the Japanese Population and Functional Analysis", *J. Pharmacology and Experimental Therapeutics* 302(2):804-813 (2002).

Reich et al., "Linkage disequilibrium in the human genome", *Nature* 411:199-204 (2001).

Stephens et al., "Haplotype Variation and Linkage Disequilibrium in 313 Human Genes", *Science* 293:489-493 (2001).

Tamai et al., Molecular Identification and Characterization of Novel Members of the Human Organic Anion Transporter (OATP) Family, *Biochemical and Biophysical Research Communications* 273:251-260 (2000).

Tirona et al., "Pharmacogenomics of organic anion-transporting polypeptides (OATP)", *Advanced Drug Delivery Reviews* 54:1343-1352 (2002).

Tirona et al., "Polymorphisms in *OATP-C*. Identification of multiple allelic variants associated with altered transport activity among European- and African-Americans", *J. Biol. Chem.* 276(38):35669-35675 (2001).

Toivonen et al., "Data Mining Applied to Linkage Disequilibrium Mapping", *Am. J. Hum. Genet.* 67:133-145 (2000).

Weiss et al., "Linkage disequilibrium and the mapping of complex human traits", *Trends in Genetics* 18:19-24 (2002).

Zhang and Zhao, "Linkage Disequilibrium Mapping with Genotype Data", *Genetic Epidemiology* 22:66-77 (2002).

* cited by examiner

SEQUENCE LISTING

<160> NUMBER OF SEQ ID NOS: 5

<210> SEQ ID NO 1
<211> LENGTH: 691
<212> TYPE: PRT
<213> ORGANISM: Homo Sapiens

<400> SEQUENCE: 1

```
Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
            100                 105                 110

Leu Pro His Phe Phe Met Gly Tyr Tyr Arg Tyr Ser Lys Glu Thr Asn
        115                 120                 125

Ile Asn Ser Ser Glu Asn Ser Thr Ser Thr Leu Ser Thr Cys Leu Ile
```

```
                130                 135                 140
Asn Gln Ile Leu Ser Leu Asn Arg Ala Ser Pro Glu Ile Val Gly Lys
145                 150                 155                 160

Gly Cys Leu Lys Glu Ser Gly Ser Tyr Met Trp Ile Tyr Val Phe Met
                165                 170                 175

Gly Asn Met Leu Arg Gly Ile Gly Glu Thr Pro Ile Val Pro Leu Gly
                180                 185                 190

Leu Ser Tyr Ile Asp Asp Phe Ala Lys Glu Gly His Ser Ser Leu Tyr
                195                 200                 205

Leu Gly Ile Leu Asn Ala Ile Ala Met Ile Gly Pro Ile Ile Gly Phe
210                 215                 220

Thr Leu Gly Ser Leu Phe Ser Lys Met Tyr Val Asp Ile Gly Tyr Val
225                 230                 235                 240

Asp Leu Ser Thr Ile Arg Ile Thr Pro Thr Asp Ser Arg Trp Val Gly
                245                 250                 255

Ala Trp Trp Leu Asn Phe Leu Val Ser Gly Leu Phe Ser Ile Ile Ser
                260                 265                 270

Ser Ile Pro Phe Phe Phe Leu Pro Gln Thr Pro Asn Lys Pro Gln Lys
                275                 280                 285

Glu Arg Lys Ala Ser Leu Ser Leu His Val Leu Glu Thr Asn Asp Glu
                290                 295                 300

Lys Asp Gln Thr Ala Asn Leu Thr Asn Gln Gly Lys Asn Ile Thr Lys
305                 310                 315                 320

Asn Val Thr Gly Phe Phe Gln Ser Phe Lys Ser Ile Leu Thr Asn Pro
                325                 330                 335

Leu Tyr Val Met Phe Val Leu Leu Thr Leu Leu Gln Val Ser Ser Tyr
                340                 345                 350

Ile Gly Ala Phe Thr Tyr Val Phe Lys Tyr Val Glu Gln Gln Tyr Gly
                355                 360                 365

Gln Pro Ser Ser Lys Ala Asn Ile Leu Leu Gly Val Ile Thr Ile Pro
                370                 375                 380

Ile Phe Ala Ser Gly Met Phe Leu Gly Gly Tyr Ile Ile Lys Lys Phe
385                 390                 395                 400

Lys Leu Asn Thr Val Gly Ile Ala Lys Phe Ser Cys Phe Thr Ala Val
                405                 410                 415

Met Ser Leu Ser Phe Tyr Leu Leu Tyr Phe Phe Ile Leu Cys Glu Asn
                420                 425                 430

Lys Ser Val Ala Gly Leu Thr Met Thr Tyr Asp Gly Asn Asn Pro Val
                435                 440                 445

Thr Ser His Arg Asp Val Pro Leu Ser Tyr Cys Asn Ser Asp Cys Asn
450                 455                 460

Cys Asp Glu Ser Gln Trp Glu Pro Val Cys Gly Asn Asn Gly Ile Thr
465                 470                 475                 480

Tyr Ile Ser Pro Cys Leu Ala Gly Cys Lys Ser Ser Gly Asn Lys
                485                 490                 495

Lys Pro Ile Val Phe Tyr Asn Cys Ser Cys Leu Glu Val Thr Gly Leu
                500                 505                 510

Gln Asn Arg Asn Tyr Ser Ala His Leu Gly Glu Cys Pro Arg Asp Asp
                515                 520                 525

Ala Cys Thr Arg Lys Phe Tyr Phe Val Ala Ile Gln Val Leu Asn
                530                 535                 540

Leu Phe Phe Ser Ala Leu Gly Gly Thr Ser His Val Met Leu Ile Val
545                 550                 555                 560
```

-continued

```
Lys Ile Val Gln Pro Glu Leu Lys Ser Leu Ala Leu Gly Phe His Ser
                565                 570                 575

Met Val Ile Arg Ala Leu Gly Gly Ile Leu Ala Pro Ile Tyr Phe Gly
                580                 585                 590

Ala Leu Ile Asp Thr Thr Cys Ile Lys Trp Ser Thr Asn Asn Cys Gly
                595                 600                 605

Thr Arg Gly Ser Cys Arg Thr Tyr Asn Ser Thr Ser Phe Ser Arg Val
            610                 615                 620

Tyr Leu Gly Leu Ser Ser Met Leu Arg Val Ser Ser Leu Val Leu Tyr
625                 630                 635                 640

Ile Ile Leu Ile Tyr Ala Met Lys Lys Tyr Gln Glu Lys Asp Ile
                645                 650                 655

Asn Ala Ser Glu Asn Gly Ser Val Met Asp Glu Ala Asn Leu Glu Ser
                660                 665                 670

Leu Asn Lys Asn Lys His Phe Val Pro Ser Ala Gly Ala Asp Ser Glu
                675                 680                 685

Thr His Cys
    690

<210> SEQ ID NO 2
<211> LENGTH: 2050
<212> TYPE: DNA
<213> ORGANISM: Homo Sapiens

<400> SEQUENCE: 2
atctcagaga ttttatttgt attcatttaa tataaattaa ctgctctaaa atttataata     60
tgcaaatatc atacaattaa tctaattagg tgttgaatct ataatgtgcc aggcattatg    120
taaggcactt tacatacact aaatctttat tccaaatata gacttcttac tttatagatg    180
agtgcactga tgctcagaaa tggtaaataa cctactgatg tttatactgc tggcaggtag    240
cagagacata tcggcattta agtctttcag acttcaaagg ccatgatatt tcatcagagc    300
tgtgatagcc gttcctgaaa aaatatcag ctgattcttt aaatcaattt ttgtcatcta    360
actgatgcgt ggctgttagc ataatattga tcttgaaaga tgttttgcaa catctttccc    420
ctggtgtact cttgtttttc catgatccca caaaatgagc agtctaatta tttacacaat    480
taggaagaga aaaggggcac agagaatgct cttTgacctc tgaaaatatt ggagaatttt    540
acaactggca cctttagctc aggattataa aggttgttag ttagtttgta ctgttttatc    600
ttcattgtat ataatatata tattagtctc caaacatgtt gatgtgtttt caatgaaatg    660
gatgtctgag gagaaaacca ttagcctgag aaaacccaaa ctgtattccc attgtgaata    720
aaaggaagtc cataaaaatg atggaaaatg ttctgcattc ctgttatgat atcaaaatct    780
ggcagtacat gaaaattttt caaagtgctt atttaacagg cataatcttt ggtctcctga    840
gccagaatct gctgggtatg ggactggatt gctattttga caactcgcca gtagattctt    900
actcagcaga gtatttggaa gccttactct aatattttgg ccttggttct acatttctca    960
gttctgcaca gtcattcttc ccctctacac tactctttag tttgtctcat gattccaata   1020
ctctcaataa ttaaccaaga atagaactaa tcaatcagat aactgtggca cagacatcaa   1080
atacattttg ctgcaaccat atcaacaaat gtcccatgaa tgataagggg taaccatatt   1140
ctcatatatg catcctcaca ttaccacata tatatgtg catatgtgta tacaggtaaa    1200
agtgtgtata tatgtataca tgtatgtttt tgtgtatata catacatata tcttcacact   1260
tttctgaaat atatatattt atgtgagaga agggtctgta cttTatttca gaagagagct   1320
```

```
taatgtccaa ggtataattg agagtctaaa atgtttgagt tattgaatta attaaacttc    1380
atctctactc aagaaaactt ttaactgagt taagctcttc ctttctccac aagtcaagtc    1440
aataaaagga aactgtgata ttaataattc tttcctgttt tgatgtaaag aatctatcgc    1500
ataaagcagt cttaattttc atcattcaga aaaatggtct tgcagttaat tgggactctc    1560
ttattccagg tggtatctcc agtctccata cataccacgt tagaaccata cttatgtacc    1620
aagcaaagag ggtatatttt aattttttaaa tgccaatgta acctgtaggc atattttta    1680 tttgtcttaa attatttcct atttggaagt tttaaatacc tggaataatt tattgtactc    1740
atatttttaa agaaaaaaat cttatgccac caacttaatt gaataaacaa gtaaaagcca    1800
ttcccaaaag taaggtttac ttgttaagat taacaaaaaa taatgtgaga attctgagaa    1860
atataatctt taaatattgg caactggagt gaactcttaa aactaactag gttttatatg    1920
tttgactaga gcaatgacat aataaggtgg ttaatcatca ctggacttgt tttcaaaaag    1980
ccaactactt taagaggaat aaagggtgga cttgttgcag ttgctgtagg attctaaatc    2040
caggtaagaa                                                          2050

<210> SEQ ID NO 3
<211> LENGTH: 2830
<212> TYPE: DNA
<213> ORGANISM: Homo Sapiens

<400> SEQUENCE: 3
cggacgcgtg ggcggacgcg tgggtcgccc acgcgtccga cttgttgcag ttgctgtagg      60
attctaaatc caggtgattg tttcaaactg agcatcaaca acaaaaacat ttgtatgata     120
tctatatttc aatcatggac caaaatcaac atttgaataa acagcagag gcacaacctt      180 cagagaataa gaaaacaaga tactgcaatg gattgaagat gttcttggca gctctgtcac     240
tcagctttat tgctaagaca ctaggtgcaa ttattatgaa aagttccatc attcatatag     300
aacggagatt tgagatatcc tcttctcttg ttggttttat tgacggaagc tttgaaattg     360
gaaatttgct tgtgattgta tttgtgagtt actttggatc caaactacat agaccaaagt     420
taattggaat cggttgtttc attatgggaa ttggaggtgt tttgactgct tgccacatt      480 tcttcatggg atattacagg tattctaaag aaactaatat cgattcatca gaaaattcaa     540
catcgacctt atccacttgt ttaattaatc aaattttatc actcaataga gcatcacctg     600
agatagtggg aaaaggttgt ttaaaggaat ctgggtcata catgtggata tatgtgttca     660
tgggtaatat gcttcgtgga atagggga gactcccatagt accattgggg ctttcttaca     720
ttgatgattt cgctaaagaa ggacattctt ctttgtattt aggtatattg aatgcaatag     780
caatgattgg tccaatcatt ggctttaccc tgggatctct gttttctaaa atgtacgtgg     840
atattggata tgtagatcta agcactatca ggataactcc tactgattct cgatgggttg     900
gagcttggtg gcttaatttc cttgtgtctg gactattctc cattatttct tccataccat     960
tcttttcctt gccccaaact ccaaatacaaa cacaaaaaga aagaaaagct tcactgtctt    1020
tgcatgtgct ggaaacaaat gatgaaaagg atcaaacagc taatttgacc aatcaaggaa    1080
aaaatattac caaaaatgtg actgttttt tccagtctttt taaagcatc cttactaatc     1140 ccctgtatgt tatgtttgtg cttttgacgt tgttacaagt aagcagctat attggtgctt    1200
ttacttatgt cttcaaatac gtagagcaac agtatggtca gccttcatct aaggctaaca    1260
tcttattggg agtcataacc ataccctattt ttgcaagtgg aatgttttta ggaggatata    1320
```

-continued

```
tcattaaaaa attcaaactg aacaccgttg gaattgccaa attctcatgt tttactgctg    1380
tgatgtcatt gtccttttac ctattatatt ttttcatact ctgtgaaaac aaatcagttg    1440
ccggactaac catgacctat gatggaaata atccagtgac atctcataga gatgtaccac    1500
tttcttattg caactcagac tgcaattgtg atgaaagtca atgggaacca gtctgtggaa    1560
acaatggaat aacttacatc tcaccctgtc tagcaggttg caaatcttca agtggcaata    1620
aaaagcctat agtgttttac aactgcagtt gtttggaagt aactggtctc cagaacagaa    1680
attactcagc ccatttgggt gaatgcccaa gagatgatgc ttgtacaagg aaattttact    1740
tttttgttgc aatacaagtc ttgaatttat ttttctctgc acttggaggc acctcacatg    1800
tcatgctgat tgttaaaatt gttcaacctg aattgaaatc acttgcactg ggtttccact    1860
caatggttat acgagcacta ggaggaattc tagctccaat atattttggg gctctgattg    1920
atacaacgtg tataaagtgg tccaccaaca actgtggcac acgtgggtca tgtaggacat    1980
ataattccac atcattttca agggtctact tgggcttgtc ttcaatgtta agagtctcat    2040
cacttgtttt atatattata ttaatttatg ccatgaagaa aaaatatcaa gagaaagata    2100
tcaatgcatc agaaaatgga agtgtcatgg atgaagcaaa cttagaatcc ttaaataaaa    2160
ataaacattt tgtcccttct gctggggcag atagtgaaac acattgttaa ggggagaaaa    2220
aaaagccact ctgcttctgt gtttccaaac agcattgcat tgattcagta agatgttatt    2280
tttgaggagt tcctggtcct ttcactaaga atttccacat cttttatggt ggaagtataa    2340
ataagcctat gaacttataa taaacaaac tgtaggtaga aaaaatgaga gtactcattg    2400
ttacattata gctacatatt tgtggttaag gttagactat atgatccata caaattaaag    2460
tgagagacat ggttactgtg taataaaaga aaaaatactt gttcaggtaa ttctaattct    2520
taataaaaca aatgagtatc atacaggtag aggttaaaaa ggaggagcta gattcatatc    2580
ctaagtaaag agaaatgcct agtgtctatt ttattaaaca aacaaacaca gagtttgaac    2640
tataatacta aggcctgaag tctagcttgg atatatgcta caataatatc tgttactcac    2700
ataaaattat atatttcaca gactttatca atgtataatt aacaattatc ttgtttaagt    2760
aaatttagaa tacatttaag tattgtggaa gaaataaaga cattccaata tttgcaaaaa    2820
aaaaaaaaaa                                                           2830
```

<210> SEQ ID NO 4
<211> LENGTH: 691
<212> TYPE: PRT
<213> ORGANISM: Homo Sapiens

<400> SEQUENCE: 4

```
Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
```

-continued

```
                100                 105                 110
Leu Pro His Phe Phe Met Gly Tyr Tyr Arg Tyr Ser Lys Glu Thr Asn
            115                 120                 125
Ile Asp Ser Ser Glu Asn Ser Thr Ser Thr Leu Ser Thr Cys Leu Ile
130                 135                 140
Asn Gln Ile Leu Ser Leu Asn Arg Ala Ser Pro Glu Ile Val Gly Lys
145                 150                 155                 160
Gly Cys Leu Lys Glu Ser Gly Ser Tyr Met Trp Ile Tyr Ala Phe Met
                165                 170                 175
Gly Asn Met Leu Arg Gly Ile Gly Glu Thr Pro Ile Val Pro Leu Gly
            180                 185                 190
Leu Ser Tyr Ile Asp Asp Phe Ala Lys Glu Gly His Ser Ser Leu Tyr
        195                 200                 205
Leu Gly Ile Leu Asn Ala Ile Ala Met Ile Gly Pro Ile Ile Gly Phe
    210                 215                 220
Thr Leu Gly Ser Leu Phe Ser Lys Met Tyr Val Asp Ile Gly Tyr Val
225                 230                 235                 240
Asp Leu Ser Thr Ile Arg Ile Thr Pro Thr Asp Ser Arg Trp Val Gly
                245                 250                 255
Ala Trp Trp Leu Asn Phe Leu Val Ser Gly Leu Phe Ser Ile Ile Ser
            260                 265                 270
Ser Ile Pro Phe Phe Phe Leu Pro Gln Thr Pro Asn Lys Pro Gln Lys
        275                 280                 285
Glu Arg Lys Ala Ser Leu Ser Leu His Val Leu Glu Thr Asn Asp Glu
    290                 295                 300
Lys Asp Gln Thr Ala Asn Leu Thr Asn Gln Gly Lys Asn Ile Thr Lys
305                 310                 315                 320
Asn Val Thr Gly Phe Phe Gln Ser Phe Lys Ser Ile Leu Thr Asn Pro
                325                 330                 335
Leu Tyr Val Met Phe Val Leu Leu Thr Leu Leu Gln Val Ser Ser Tyr
            340                 345                 350
Ile Gly Ala Phe Thr Tyr Val Phe Lys Tyr Val Glu Gln Gln Tyr Gly
        355                 360                 365
Gln Pro Ser Ser Lys Ala Asn Ile Leu Leu Gly Val Ile Thr Ile Pro
    370                 375                 380
Ile Phe Ala Ser Gly Met Phe Leu Gly Gly Tyr Ile Ile Lys Lys Phe
385                 390                 395                 400
Lys Leu Asn Thr Val Gly Ile Ala Lys Phe Ser Cys Phe Thr Ala Val
                405                 410                 415
Met Ser Leu Ser Phe Tyr Leu Leu Tyr Phe Phe Ile Leu Cys Glu Asn
            420                 425                 430
Lys Ser Val Ala Gly Leu Thr Met Thr Tyr Asp Gly Asn Asn Pro Val
        435                 440                 445
Thr Ser His Arg Asp Val Pro Leu Ser Tyr Cys Asn Ser Asp Cys Asn
    450                 455                 460
Cys Asp Glu Ser Gln Trp Glu Pro Val Cys Gly Asn Asn Gly Ile Thr
465                 470                 475                 480
Tyr Ile Ser Pro Cys Leu Ala Gly Cys Lys Ser Ser Gly Asn Lys
                485                 490                 495
Lys Pro Ile Val Phe Tyr Asn Cys Ser Cys Leu Glu Val Thr Gly Leu
            500                 505                 510
Gln Asn Arg Asn Tyr Ser Ala His Leu Gly Glu Cys Pro Arg Asp Asp
        515                 520                 525
```

-continued

```
Ala Cys Thr Arg Lys Phe Tyr Phe Val Ala Ile Gln Val Leu Asn
    530                 535                 540

Leu Phe Phe Ser Ala Leu Gly Gly Thr Ser His Val Met Leu Ile Val
545                 550                 555                 560

Lys Ile Val Gln Pro Glu Leu Lys Ser Leu Ala Leu Gly Phe His Ser
                565                 570                 575

Met Val Ile Arg Ala Leu Gly Gly Ile Leu Ala Pro Ile Tyr Phe Gly
            580                 585                 590

Ala Leu Ile Asp Thr Thr Cys Ile Lys Trp Ser Thr Asn Asn Cys Gly
        595                 600                 605

Thr Arg Gly Ser Cys Arg Thr Tyr Asn Ser Thr Ser Phe Ser Arg Val
    610                 615                 620

Tyr Leu Gly Leu Ser Ser Met Leu Arg Val Ser Ser Leu Val Leu Tyr
625                 630                 635                 640

Ile Ile Leu Ile Tyr Ala Met Lys Lys Tyr Gln Glu Lys Asp Ile
                645                 650                 655

Asn Ala Ser Glu Asn Gly Ser Val Met Asp Glu Ala Asn Leu Glu Ser
            660                 665                 670

Leu Asn Lys Asn Lys His Phe Val Pro Ser Ala Gly Ala Asp Ser Glu
        675                 680                 685

Thr His Cys
    690

<210> SEQ ID NO 5
<211> LENGTH: 691
<212> TYPE: PRT
<213> ORGANISM: Homo Sapiens

<400> SEQUENCE: 5

Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
            100                 105                 110

Leu Pro His Phe Phe Met Gly Tyr Tyr Arg Tyr Ser Lys Glu Thr Asn
        115                 120                 125

Ile Asn Ser Ser Glu Asn Ser Thr Ser Thr Leu Ser Thr Cys Leu Ile
    130                 135                 140

Asn Gln Ile Leu Ser Leu Asn Arg Ala Ser Pro Glu Ile Val Gly Lys
145                 150                 155                 160

Gly Cys Leu Lys Glu Ser Gly Ser Tyr Met Trp Ile Tyr Ala Phe Met
                165                 170                 175

Gly Asn Met Leu Arg Gly Ile Gly Glu Thr Pro Ile Val Pro Leu Gly
            180                 185                 190

Leu Ser Tyr Ile Asp Asp Phe Ala Lys Glu Gly His Ser Ser Leu Tyr
```

-continued

```
            195                 200                 205
Leu Gly Ile Leu Asn Ala Ile Ala Met Ile Gly Pro Ile Ile Gly Phe
            210                 215                 220
Thr Leu Gly Ser Leu Phe Ser Lys Met Tyr Val Asp Ile Gly Tyr Val
225                 230                 235                 240
Asp Leu Ser Thr Ile Arg Ile Thr Pro Thr Asp Ser Arg Trp Val Gly
                    245                 250                 255
Ala Trp Trp Leu Asn Phe Leu Val Ser Gly Leu Phe Ser Ile Ile Ser
                260                 265                 270
Ser Ile Pro Phe Phe Phe Leu Pro Gln Thr Pro Asn Lys Pro Gln Lys
            275                 280                 285
Glu Arg Lys Ala Ser Leu Ser Leu His Val Leu Glu Thr Asn Asp Glu
        290                 295                 300
Lys Asp Gln Thr Ala Asn Leu Thr Asn Gln Gly Lys Asn Ile Thr Lys
305                 310                 315                 320
Asn Val Thr Gly Phe Phe Gln Ser Phe Lys Ser Ile Leu Thr Asn Pro
                    325                 330                 335
Leu Tyr Val Met Phe Val Leu Leu Thr Leu Leu Gln Val Ser Ser Tyr
                340                 345                 350
Ile Gly Ala Phe Thr Tyr Val Phe Lys Tyr Val Glu Gln Gln Tyr Gly
            355                 360                 365
Gln Pro Ser Ser Lys Ala Asn Ile Leu Leu Gly Val Ile Thr Ile Pro
        370                 375                 380
Ile Phe Ala Ser Gly Met Phe Leu Gly Gly Tyr Ile Ile Lys Lys Phe
385                 390                 395                 400
Lys Leu Asn Thr Val Gly Ile Ala Lys Phe Ser Cys Phe Thr Ala Val
                    405                 410                 415
Met Ser Leu Ser Phe Tyr Leu Leu Tyr Phe Phe Ile Leu Cys Glu Asn
                420                 425                 430
Lys Ser Val Ala Gly Leu Thr Met Thr Tyr Asp Gly Asn Asn Pro Val
            435                 440                 445
Thr Ser His Arg Asp Val Pro Leu Ser Tyr Cys Asn Ser Asp Cys Asn
        450                 455                 460
Cys Asp Glu Ser Gln Trp Glu Pro Val Cys Gly Asn Asn Gly Ile Thr
465                 470                 475                 480
Tyr Ile Ser Pro Cys Leu Ala Gly Cys Lys Ser Ser Gly Asn Lys
                    485                 490                 495
Lys Pro Ile Val Phe Tyr Asn Cys Ser Cys Leu Glu Val Thr Gly Leu
                500                 505                 510
Gln Asn Arg Asn Tyr Ser Ala His Leu Gly Glu Cys Pro Arg Asp Asp
            515                 520                 525
Ala Cys Thr Arg Lys Phe Tyr Phe Val Ala Ile Gln Val Leu Asn
        530                 535                 540
Leu Phe Phe Ser Ala Leu Gly Gly Thr Ser His Val Met Leu Ile Val
545                 550                 555                 560
Lys Ile Val Gln Pro Glu Leu Lys Ser Leu Ala Leu Gly Phe His Ser
                    565                 570                 575
Met Val Ile Arg Ala Leu Gly Gly Ile Leu Ala Pro Ile Tyr Phe Gly
                580                 585                 590
Ala Leu Ile Asp Thr Thr Cys Ile Lys Trp Ser Thr Asn Asn Cys Gly
            595                 600                 605
Thr Arg Gly Ser Cys Arg Thr Tyr Asn Ser Thr Ser Phe Ser Arg Val
        610                 615                 620
```

-continued

```
Tyr Leu Gly Leu Ser Ser Met Leu Arg Val Ser Ser Leu Val Leu Tyr
625                 630                 635                 640

Ile Ile Leu Ile Tyr Ala Met Lys Lys Lys Tyr Gln Glu Lys Asp Ile
                645                 650                 655

Asn Ala Ser Glu Asn Gly Ser Val Met Asp Glu Ala Asn Leu Glu Ser
            660                 665                 670

Leu Asn Lys Asn Lys His Phe Val Pro Ser Ala Gly Ala Asp Ser Glu
        675                 680                 685

Thr His Cys
    690
```

USE OF POLYMORPHISMS IN HUMAN OATP-C ASSOCIATED WITH AN EFFECT ON STATIN PHARMACOKINETICS IN HUMANS IN STATIN THERAPY

CROSS-REFERENCE TO RELATED APPLICATIONS

This application is a national phase application under 35 U.S.C. § 371 of PCT International Application No. PCT/GB2004/003236, filed Jul. 26, 2004, which claims priority to Great Britain Application Serial No. 0317592.4, filed Jul. 26, 2003. The contents of these applications are incorporated herein by reference in their entirety.

This invention relates to use of polymorphisms in human OATP-C in statin therapy because they are associated with an effect on statin pharmacokinetics (PK) in humans, especially rosuvastatin pharmacokinetics. The invention also relates to the use of OATP-C polymorphisms in predicting the efficacy and safety of statins, whose uptake in to the liver is mediated by OATP-C, especially rosuvastatin.

The OATP-C gene (sometimes called LST1, OAPT2, SLCO1B1, SLC21A6 or OATP1B1) has been cloned by four different groups, annotated and published as EMBL accession numbers AB026257 (OATP-C 2452bp), AF205071 (OATP2, 2830, SEQ ID herein), AJ132573(OATP2, 2778), and AF060500 (LST-1). Konig (2000) J Biol Chem 275, 23161-23168 describes the genomic organisation of OATP 1, 2 and 8. International patent application WO 00/08157 describes human anion transporter genes and some polymorphisms.

Na+-independent organic anion transporting polypeptide (OATP) C gene is a member of the OATP supergene family involved in multifunctional transport of organic anions. OATP-C transports a diverse range of molecules e.g. the organic anion taurocholate, conjugated steroids: DHEAS, estradiol 17β-D-glucoronide and estrone-3-sulfate, eicosanoids: $PGE_2$, thromboxane $B_2$, leukotriene $C_4$, and $E_4$, and thyroid hormones T4 and T3. OATP-C has also been shown to be involved in the transport of xenobiotics, and drugs involved in lipid lowering e.g. statins. Statins are a class of drugs which inhibit 3-hydroxy-3-methylglutaryl-coenzyme A (HMG-CoA). They are an important therapy for patients with atherosclerotic vascular diseases and are generally well tolerated, although some rare adverse events have been noted in all marketed statins. Pharmacokinetic differences between statins have been associated with differences in benefit-risk ratio (Igel (2002) J Clin Pharmacol 42:835-45).

It is generally recommended that in order to gain maximum benefit-risk ratio from statin therapy, the dose prescribed should be individualized according to goal of therapy and response. For example, the recommended usual starting dose of rosuvastatin is 10 mg once daily in patients with hypercholesterolemia and mixed dyslipidemia, although a 5-mg dose is also available. For patents with marked hypercholesterolemia (LDL-C>190 mg/dL) and aggressive lipid targets, a 20-mg starting dose may be considered. The 40-mg dose should be reserved for those patients who have not achieved goal LDL-C at 20 mg. After initiation and/or upon titration of rosuvastatin, lipid levels should be analyzed within 2 to 4 weeks and dosage adjusted accordingly.

Pravastatin is actively transported from the circulation to the liver via the OATP-C transporter (Hsiang, B. Journal of Biological Chemistry. 274(52), 37161-37168. 1999). Rosuvastatin was shown to be a substrate for OATP-C in vitro (Brown (2001) Atherosclerosis Supplements 2, pg 90, poster abstract P174). Numerous polymorphisms in OATP-C have been reported in the literature and SNP databases. Identification of SNPs in OATP-C was reported in EP1186672. Polymorphism in OATP-C has been reported by Tamai et al (2000), BBRC, 273, 251-60 and reviewed by Tirona (2002) Adv Drug Delivery Reviews 54:1343-52. Tirona showed that some OATP-C polymorphisms, including the V174A variant, were associated with reduced transport of endogenous substrates in vitro. Using a different cell system, Nozawa et al (2001) J Pharmacol Exp Ther, 302, 804-13, found that the V174A (OATPC*5) variant did not affect substrate transport. Tirona stated that the in vivo relevance of OATP-C polymorphisms remained to be determined.

Niemi et al (July 2004) Pharmacogenetics 14(7), 429-440 describes SNPs in OATPC, including promoter SNPs. The authors report a significant correlation between pravastatin PK (pharmacokinetics) and a haplotype containing a promoter SNP in a cohort of healthy volunteers.

Nishizato (2003) Clin Pharmacol Ther 73:554-65 published in-vivo data showing that the OATPC*15 allele, containing both the N130D and the V174A polymorphisms, had an effect on the pharmacokinetics of pravastatin in Japanese healthy volunteers. Nishizato did not report the effect of the OATP-C*5 allele, which has not been detected in the Japanese population to date, and stated that large clinical studies are needed to investigate this effect. There have been no pharmacokinetic studies in patients taking pravastatin. There have been no pharmacogenetic studies on healthy volunteers or patients taking rosuvastatin. Hence, the observations of Nishizato et al performed in Japanese healthy volunteers are not predictive of the PK profiles of patients or of other populations, or of the PK profiles of other statins which may differ in the affinity for different transporters.

Population PK modelling analyses, using data collected by AstraZeneca in the rosuvastatin clinical development programme, confirm that healthy volunteers and patients differ with respect to their distribution of rosuvastatin. Patients receiving statins for lipid lowering may be on other drugs transported by OATP-C and drug-drug interactions may affect the PK profile of statins (Int J Clin Pharmacol Ther (2002), 40, 439-50). Patients prescribed statins may also have other liver and kidney complications affecting the distribution and excretion of statins. There is an entire chapter in the textbook Clinical Pharmacokinetics (Chapter 16, pages 248-266 in $3_{rd}$ edition 1995, Rowland & Tozer, published by Williams & Wilkins) which begins:

"Disease is a major source of variability in drug response. For many diseases this is due primarily to differences in pharmacokinetics . . . ."

Hence there is a need to identify which polymorphisms in OATP-C have an effect on in vivo pharmacokinetics of rosuvastatin and other statins in patients with vascular disease or a predisposition thereto. Our invention is based on the discovery that the V174A polymorphism and/or a polymorphism in linkage disequilibrium therewith has a statistically significant effect on statin pharmacokinetics in patients. The V174A polymorphism may affect the response to statins, especially rosuvastatin.

According to one aspect of the invention there is provided a method of diagnosis comprising:

(a) providing a biological sample from a human identified as being in need of treatment with a therapeutic agent that is transported by OATP-C, wherein the sample comprises a nucleic acid encoding OATP-C;

(b) testing the nucleic acid for the presence, on at least one allele, of either (i) a codon encoding alanine at the position corresponding to position 174 of SEQ ID NO:1, or (ii) an allele of a polymorphism in linkage disequilibrium with (i); and (c) if either (i) or (ii) is found in at least one allele, diagnosing the human as likely to have reduced ability to transport the therapeutic agent into cells.

Preferably the polymorphism of (b)(ii) is −26A>G, −118A>C, −309T>C, −878A>G, −903C>T, −1054G>T, −1215T>A, or −1558T>C, all of SEQ ID NO:2; or T2122G, C2158T, A2525C, or G2651A, all of SEQ ID NO:3.

More preferably the polymorphism of (b)(ii) is −118A>C or −1558T>C of SEQ ID NO:2. Alleles of polymorphisms at −118 and −1558 are in significant linkage disequilibrium with the alanine allele at position 174 of SEQ ID NO:1 (p=0.009 and 0.025 respectively, analysed by the ASSOCIATE program, see Ott J (1999) Analysis of human genetic linkage, 3rd edition. Johns Hopkins University Press Baltimore).

Most preferably the polymorphism of (b)(ii) is −118A>C of SEQ ID NO:2; Example 2 hereinbelow describes the functional effect of this polymorphism.

For any variant position, for example −26A>G, this indicates that at position 26 A is replaced by G. This can be tested by either detecting G at that position or by detecting that there is not an A at that position. Similar considerations apply to any variant position.

Preferably the therapeutic agent is a statin, the human is being treated with one dose level of statin and step (c) further comprises diagnosing the human as suitable for titration to another higher statin dose level comprising monitoring for a decrease in benefit-risk ratio resulting from the reduced ability to transport the statin into cells.

More preferably the therapeutic agent is rosuvastatin.

In another embodiment the therapeutic agent is one of atorvastatin, cerivastatin, fluvastatin, pravastatin, or simvastatin.

Preferably the human is being treated with at least 5mg of a rosuvastatin daily. More preferably the human is being treated with at least 10 mg of a rosuvastatin daily. More preferably the human is being treated with at least 20 mg of a rosuvastatin daily. More preferably the human is being treated with at least 40 mg of a rosuvastatin daily.

According to another aspect of the invention there is provided a method of diagnosis comprising:

(a) providing a biological sample from a human identified as being in need of treatment with a therapeutic agent that is transported into cells by OATP-C wherein the sample comprises an OATP-C polypeptide;

(b) determining whether the amino acid of OATP-C corresponding to position 174 of SEQ ID NO:1 is a valine; and (c) if the amino acid is not a valine, diagnosing the human as likely to have a reduced ability to transport the therapeutic agent into cells.

Preferably the therapeutic agent is a statin, the human is being treated with one dose level of statin and step (c) further comprises diagnosing the human as suitable for titration to another higher statin dose level comprising monitoring for a decrease in benefit-risk ratio resulting from the reduced ability to transport the statin into cells.

Preferably the method further comprises measurement of the level of OATPC polypeptide with valine and/or alanine at position 174 whereby to determine the presence or absence of −118A>C polymorphism in OATP-C nucleic acid.

Preferably the method is one further comprising measuring the level of OATP-C polypeptide for presence or absence of OATP-C*15 allele whereby to determine the presence or absence of −118A>C polymorphism in OATP-C nucleic acid.

Without wishing to be bound by theoretical considerations, the level of protein expression of each of the different allelic forms of OATPC may be determined where the level of expression of the Ala174 variant is increased due to enhanced promoter activity in the presence of the linked −118 C promoter variant. For example, by determining the ratio of Val174: Ala174 protein isoforms, where the Ala 174 reduced function protein is present in excess of the Val 174 normal function transporter in subjects heterozygote at position 174 in the amino acid sequence. In another example, by determining the absolute level of OATPC expression in Ala174 homozygote subjects, and comparing the absolute expression level to that of the population mean for subjects homozygote for the Val174 variant where the relative expression of the Ala 174 allele is increased in the presence of the −118 C linked promoter allele, as compared to Ala 174 alleles linked to the −118 A promoter variant. In another example, by determining the absolute level of OATPC expression in Ala174 homozygote subjects, and comparing the absolute expression level to that of the population mean, Ala174 homozygote subjects, with the highest levels of OATPC expression, may be predicted to have one or more copies of the −118 C promoter variant through the increased transcription activity of the minor allelic form of the OATPC promoter.

Preferably the amino acid at position 174 is determined to be alanine. More preferably the therapeutic agent is rosuvastatin.

In another embodiment the therapeutic agent is one of atorvastatin, cerivastatin, fluvastatin, pravastatin, or simvastatin.

Preferably the human is being treated with at least 5 mg of a rosuvastatin daily. More preferably the human is being treated with at least 10 mg of a rosuvastatin daily. More preferably the human is being treated with at least 20 mg of a rosuvastatin daily. More preferably the human is being treated with at least 40 mg of a rosuvastatin daily.

According to one aspect of the present invention there is provided an in vitro diagnostic method to identify a patient potentially requiring a statin dose level above the minimum recommended dose level or to identify a patient in which titration to a statin dose level above the minimum recommended dose level should be monitored in which the method comprises testing a biological sample from the patient for presence of alanine at position 174 of OATP-C polypeptide and/or a polymorphism in linkage disequilibrium therewith.

The biological sample is conveniently a sample of blood, bronchoalveolar lavage fluid, sputum, liver or other body fluid or tissue obtained from an individual. It will be appreciated that the test sample may equally be a nucleic acid sequence corresponding to the sequence in the test sample, that is to say that all or a part of the region in the sample nucleic acid may firstly be amplified using any convenient technique e.g. PCR, before analysis of allelic variation. Preferably the patient is tested for presence of alanine at position 174 either through analysis of polypeptide directly or through analysis of genetic material encoding the polypeptide. As patients carry 2 copies of the OATPC gene they may be homozygous or heterozygous genotype. Polymorphisms in linkage disequilibrium with alanine at 174 may be tested as an alternative to determining the presence of alanine at 174 directly.

It will be apparent to the person skilled in the art that there are a large number of analytical procedures which may be used to detect the presence or absence of variant nucleotides at one or more polymorphic positions of the invention. In general, the detection of allelic variation requires a mutation discrimination technique, optionally an amplification reaction and optionally a signal generation system. Table 1 lists a number of mutation detection techniques, some based on the PCR. These may be used in combination with a number of signal generation systems, a selection of which is listed in Table 2. Further amplification techniques are listed in Table 3.

Many current methods for the detection of allelic variation are reviewed by Nollau et al., Clin. Chem 43, 1114-1120, 1997; and in standard textbooks, for example "Laboratory Protocols for Mutation Detection", Ed. by U. Landegren, Oxford University Press, 1996 and "PCR", $2^{nd}$ Edition by Newton & Graham, BIOS Scientific Publishers Limited, 1997.

Abbreviations:

| | |
|---|---|
| ALEX ™ | Amplification refractory mutation system linear extension |
| APEX | Arrayed primer extension |
| ARMS ™ | Amplification refractory mutation system |
| b-DNA | Branched DNA |
| bp | base pair |
| CMC | Chemical mismatch cleavage |
| COPS | Competitive oligonucleotide priming system |
| DGGE | Denaturing gradient gel electrophoresis |
| FRET | Fluorescence resonance energy transfer |
| LCR | Ligase chain reaction |
| MASDA | Multiple allele specific diagnostic assay |
| NASBA | Nucleic acid sequence based amplification |
| OLA | Oligonucleotide ligation assay |
| PCR | Polymerase chain reaction |
| PTT | Protein truncation test |
| RFLP | Restriction fragment length polymorphism |
| SDA | Strand displacement amplification |
| SNP | Single nucleotide polymorphism |
| SSCP | Single-strand conformation polymorphism analysis |
| SSR | Self sustained replication |
| TGGE | Temperature gradient gel electrophoresis |

Table 1—Mutation Detection Techniques
General: DNA sequencing, Sequencing by hybridisation
Scanning: PTT*, SSCP, DGGE, TGGE, Cleavase, Heteroduplex analysis, CMC, Enzymatic mismatch cleavage
*Note: not useful for detection of promoter polymorphisms.

Hybridisation Based
  Solid phase hybridisation: Dot blots, MASDA, Reverse dot blots, Oligonucleotide arrays (DNA Chips)
  Solution phase hybridisation: Taqman™—U.S. Pat. No. 5,210,015 & U.S. Pat. No. 5,487,972 (Hoffmann-La Roche), Molecular Beacons—Tyagi et al (1996), Nature Biotechnology, 14, 303; WO 95/13399 (Public Health Inst., New York)
Extension Based: ARMS™, ALEX™—European Patent No. EP 332435 B1 (Zeneca Limited), COPS—Gibbs et al (1989), Nucleic Acids Research, 17, 2347.
Incorporation Based: Mini-sequencing, APEX.
Restriction Enzyme Based: RFLP, Restriction site generating PCR
Ligation Based: OLA
Other: Invader assay Table 2—Signal Generation or Detection Systems
Fluorescence: FRET, Fluorescence quenching, Fluorescence polarisation—United Kingdom Patent No. 2228998 (Zeneca Limited)
Other: Chemiluminescence, Electrochemiluminescence, Raman, Radioactivity, Colorimetric, Hybridisation protection assay, Mass spectrometry Table 3—Further Amplification Methods
SSR, NASBA, LCR, SDA, b-DNA Table 4—Protein Variation Detection Methods
Immunoassay
Immunohistology
Peptide Sequencing
  Preferred mutation detection techniques include ARMS™, ALEX™, COPS, Taqman, Molecular Beacons, RFLP, and restriction site based PCR and FRET techniques. Immunoassay techniques are known in the art e.g. A Practical Guide to ELISA by D M Kemeny, Pergamon Press 1991; Principles and Practice of Immunoassay, $2^{nd}$ edition, C P Price & D J Newman, 1997, published by Stockton Press in USA & Canada and by Macmillan Reference in the United Kingdom. Histological techniques are described in Theory and Practice of Histological Techniques by J D Bancroft & A Stevens, $4^{th}$ Edition, Churchill Livingstone, 1996. Protein sequencing is described in Laboratory Techniques in Biochemistry and Molecular Biology, Volume 9, Sequencing of Proteins and Peptides, G Allen, $2^{nd}$ revised edition, Elsevier, 1989.

Particularly preferred methods include ARMS™ and RFLP based methods. ARMS™ is an especially preferred method.

Antibodies can be prepared using any suitable method. For example, purified polypeptide may be utilized to prepare specific antibodies. The term "antibodies" is meant to include polyclonal antibodies, monoclonal antibodies, and the various types of antibody constructs such as for example $F(ab')_2$, Fab and single chain Fv. Antibodies are defined to be specifically binding if they bind the allelic variant of OATP-C with a $K_a$ of greater than or equal to about $10^7$ $M^{-1}$. Affinity of binding can be determined using conventional techniques, for example those described by Scatchard et al., Ann. N.Y Acad. Sci., 51:660 (1949).

Polyclonal antibodies can be readily generated from a variety of sources, for example, horses, cows, goats, sheep, dogs, chickens, rabbits, mice or rats, using procedures that are well-known in the art. In general, antigen is administered to the host animal typically through parenteral injection. The immunogenicity of antigen may be enhanced through the use of an adjuvant, for example, Freund's complete or incomplete adjuvant. Following booster immunizations, small samples of serum are collected and tested for reactivity to antigen. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radioimmunoprecipitation, enzyme-linked immuno-sorbent assays (ELISA), dot blot assays, and sandwich assays, see U.S. Pat. Nos. 4,376,110 and 4,486,530.

Monoclonal antibodies may be readily prepared using well-known procedures, see for example, the procedures described in U.S. Pat. Nos. RE 32,011, 4,902,614, 4,543,439 and 4,411,993; Monoclonal Antibodies, Hybridomas: *A New Dimension in Biological Analyses*, Plenum Press, Kennett, McKearn, and Bechtol (eds.), (1980).

Monoclonal antibodies can be produced using alternative techniques, such as those described by Alting-Mees et al, "Monoclonal Antibody Expression Libraries: A Rapid Alternative to Hybridomas", *Strategies in Molecular Biology* 3: 1-9 (1990) which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7: 394 (1989).

Once isolated and purified, the antibodies may be used to detect the presence of particular polypeptide variants in a sample using established assay protocols, see for example "A Practical Guide to ELISA" by D. M. Kemeny, Pergamon Press, Oxford, England.

Statins already approved for use in humans include atorvastatin, cerivastatin, fluvastatin, pravastatin and simvastatin. The reader is referred to the following references for further information: Drugs and Therapy Perspectives (12May 1997), 9: 1-6; Chong (1997) Pharmacotherapy 17: 1157-1177; Kellick (1997) Formulary 32: 352; Kathawala (1991) Medicinal Research Reviews, 11: 121-146; Jahng (1995) Drugs of the Future 20: 387-404, and Current Opinion in Lipidology, (1997), 8, 362-368. A preferred statin drug is compound 3a (S-4522) in Watanabe (1997) Bioorganic and Medicinal Chemistry 5: 437-444; now called rosuvastatin, see Olsson (2001) American Journal of Cardiology, 87, supplement 1, 33-36.

Preferably the statin is rosuvastatin. Preferably the patient is prescribed at least 40 mg of rosuvastatin daily, more preferably the patient is prescribed at least 60 mg of rosuvastatin daily and especially the patient is prescribed at least 80 mg of rosuvastatin daily.

Preferably the patient is additionally tested for presence of valine at position 174 of OATP-C polypeptide whereby presence of both valine and alanine at position 174 indicates heterozygosity at this locus.

Preferably the polymorphism in linkage disequilibrium with alanine174 OATP-C is selected from at least one of:
a) Asp130 OATP-C; or
b) consensus NF1 transcription factor binding sites at positions −26A>G or −118A>C relative to the transcription initiation site (SEQ ID No 2); or
c) −309T>C, −878A>G, −903C>T, −1054G>T, −1215T>A or −1558 T>C, where nucleotide positions are relative to the transcription initiation site (SEQ ID No 2); or
d) polymorphisms in the 3'UTR region of the OATP-C gene selected from T2122G, C2158T, A2525C, and G2651A, where the nucleotide position is relative to the ATG, and the A of the ATG is nucleotide +1 (sequence accession number AF205071 and SEQ ID No 3)

The transcription initiation site is defined in Jung, D. 2001 Journal of Biological Chemistry. 276(40), 37206-37214.

In one embodiment the biological sample is tested for presence of an amino acid at a position of the OATP-C polypeptide through analysis of genetic material encoding the polypeptide.

Another aspect of the invention provides an in vitro method of monitoring a patient for an adverse event related to statin therapy wherein the method comprises testing a biological sample from the patient for a parameter indicative of an adverse event and wherein the patient is selected for such monitoring by a method described herein.

Preferably the patient is OATPC*5 or *15 genotype. As patients carry 2 copies of the OATPC gene they may be homozygous or heterozygous genotype.

According to another aspect of the present invention there is provided a method for the detection of a polymorphism in OATPC in a human, which method comprises determining the sequence of the human at at least one of the following polymorphic positions:
a) consensus NF1 transcription factor binding sites at positions −26A>G or −118A>C relative to the transcription initiation site; or
b) −309T>C, −878A>G, −903C>T, −1054G>T, −1215T>A or −1558 T>C, where nucleotide positions are relative to the transcription initiation site; or
c) polymorphisms in the 3'UTR region of the OATP-C gene selected from T2122G, C2158T, A2525C, and G2651A, where the nucleotide position is relative to the ATG, and the A of the ATG is nucleotide +1 (sequence accession number AF205071 and SEQ ID No 3).

According to another aspect of the present invention there is provided a human OATPC gene or its complementary strand comprising a variant allelic polymorphism at one or more of positions defined herein or a fragment thereof of at least 20 bases comprising at least one novel polymorphism.

According to another aspect of the present invention there is provided an allele specific primer capable of detecting a OATPC gene polymorphism, preferably at one or more of the positions as defined herein.

An allele specific primer is used, generally together with a constant primer, in an amplification reaction such as a PCR reaction, which provides the discrimination between alleles through selective amplification of one allele at a particular sequence position e.g. as used for ARMS™ assays. The allele specific primer is preferably 17-50 nucleotides, more preferably about 17-35 nucleotides, more preferably about 17-30 nucleotides.

An allele specific primer preferably corresponds exactly with the allele to be detected but derivatives thereof are also contemplated wherein about 6-8 of the nucleotides at the 3' terminus correspond with the allele to be detected and wherein up to 10, such as up to 8, 6, 4, 2, or 1 of the remaining nucleotides may be varied without significantly affecting the properties of the primer.

Primers may be manufactured using any convenient method of synthesis. Examples of such methods may be found in standard textbooks, for example "protocols for Oligonucleotides and Analogues; Synthesis and Properties," Methods in Molecular Biology Series; Volume 20; Ed. Sudhir Agrawal, Humana ISBN: 0-89603-247-7; 1993; 1$^{st}$ Edition. If required the primer(s) may be labelled to facilitate detection.

According to another aspect of the present invention there is provided an allele-specific oligonucleotide probe capable of detecting a OATPC gene polymorphism, preferably at one or more of the positions defined herein.

The allele-specific oligonucleotide probe is preferably 17-50 nucleotides, more preferably about 17-35 nucleotides, more preferably about 17-30 nucleotides.

The design of such probes will be apparent to the molecular biologist of ordinary skill. Such probes are of any convenient length such as up to 50 bases, up to 40 bases, more conveniently up to 30 bases in length, such as for example 8-25 or 8-15 bases in length. In general such probes will comprise base sequences entirely complementary to the corresponding wild type or variant locus in the gene. However, if required one or more mismatches may be introduced, provided that the discriminatory power of the oligonucleotide probe is not unduly affected. The probes of the invention may carry one or more labels to facilitate detection.

According to another aspect of the present invention there is provided an allele specific primer or an allele specific oligonucleotide probe capable of detecting a OATPC gene polymorphism at one of the positions defined herein.

According to another aspect of the present invention there is provided a diagnostic kit comprising an allele specific oligonucleotide probe of the invention and/or an allele-specific primer of the invention.

The diagnostic kits may comprise appropriate packaging and instructions for use in the methods of the invention. Such kits may further comprise appropriate buffer(s) and polymerase(s) such as thermostable polymerases, for example taq polymerase.

According to another aspect of the present invention there is provided a method of treating a patient in need of treatment with a statin in which the method comprises:
i) use of an in vitro diagnostic method to identify a patient potentially requiring a statin dose level above the minimum recommended dose level or to identify a patient in which titration to a statin dose level above the minimum recommended dose level should be monitored and in which the method comprises testing a biological sample from the patient for presence of alanine at position 174 of OATP-C polypeptide and/or a polymorphism in linkage disequilibrium therewith; and ii) administering an effective amount of the drug.

According to another aspect of the invention there is provided use of a statin in preparation of a medicament for treating a patient with vascular disease or a predisposition thereto wherein the patient is identified by an in vitro diagnostic to identify a patient potentially requiring a statin dose level above the minimum recommended dose level or to identify a patient in which titration to a statin dose level above the minimum recommended dose level should be monitored and in which the method comprises testing a biological sample from the patient for presence of alanine at position 174 of OATP-C polypeptide and/or a polymorphism in linkage disequilibrium therewith.

According to another aspect of the invention there is provided a method of classifying a patient in need of statin therapy comprising testing a biological sample from the patient for presence of alanine at position 174 of OATP-C polypeptide and/or a polymorphism in linkage disequilibrium therewith.

According to another aspect of the invention there is provided a method of identifying a patient on statin therapy that requires adverse event monitoring comprising testing a biological sample from the patient for presence of alanine at position 174 of OATP-C polypeptide and/or a polymorphism in linkage disequilibrium therewith.

"Adverse event" means the development of an undesirable medical condition or the deterioration of a pre-existing medical condition following or during exposure to a pharmaceutical product, whether or not considered causally related to the product. An undesirable medical condition can be symptoms (eg. nausea, chest pain), signs (eg. tachycardia, enlarged liver) or the abnormal results of an investigation (eg. laboratory findings, electrocardiogram).

"Linkage disequilibrium" means the occurrence of alleles at genetic loci together, more often than would be expected by chance.

"patient" means a person who is receiving medical treatment.

"Dose" means quantity to be administered at one time, such as a specified amount of medication. For rosuvastatin, the adult starting dose is usually 10 mg daily. Higher doses may be required to produce desired lipid profiles in some patients.

"Benefit Risk ratio" means the relation between the risks and benefits of a given treatment or procedure.

An acceptable risk relates to the potential for suffering disease or injury that will be tolerated by an individual in exchange for the benefits of using a substance or process that will cause such disease or injury. Acceptability of risk depends on scientific data, social, economic, and political factors, and on the perceived benefits arising from a chemical or process that creates the risk(s) in question.

According to another aspect of the invention there is provided a method of testing for an adverse event in a patient, the method comprising (a) identifying a patient who
  (i) is in need of treatment with a therapeutic agent that is transported by OATP-C, and
  (ii) has (A) an alanine at the amino acid position of OATP-C corresponding to position 174 of SEQ ID NO:1, or (B) a polymorphism in linkage disequilibrium with (A);

(b) providing a biological sample from the patient after the patient undergoes treatment with the therapeutic agent; and (c) testing the sample for a parameter indicative of an adverse event related to treatment with the therapeutic agent.

According to another aspect of the invention there is provided a method of treatment comprising:

(a) identifying a patient in need of treatment with a therapeutic agent that is transported by OATP-C;

(b) determining whether the patient has either or both of
  (i) an alanine at the amino acid position of OATP-C corresponding to position 174 of SEQ ID NO:1, or
  (ii) a polymorphism in linkage disequilibrium with (i); and (c) prescribing an appropriate dosage of the therapeutic agent.

Preferably the method further comprises:

(d) monitoring the patient for an adverse event relating to reduced transport of the therapeutic agent.

According to another aspect of the invention there is provided a method for characterizing the genotype of a human identified as being in need of a treatment with a drug transportable by OATP-C, the method comprising:

(a) providing a nucleic acid sample from the human, wherein the sample comprises a first nucleotide at a position corresponding to position 620 of SEQ ID NO:1;

(b) testing the sample to determine the identity of the first nucleotide;

(c) recording the identity of the first nucleotide in print or in a machine-readable medium; and (d) communicating the identity of the first nucleotide to the human or to the human's caregiver.

According to another aspect of the invention there is provided a method for evaluating an OATP-C gene in a human, the method comprising:

(a) receiving a request for performing a haplotype analysis of a human from a client, wherein the human is in need of treatment with a therapeutic agent transportable by OATP-C;

(b) accepting a nucleic acid sample of the human;

(c) testing the sample to determine the presence of a variant described herein; and (d) providing results of the testing to a party, thereby evaluating the OATP-C gene.

According to another aspect of the invention there is provided a method to assess the pharmacogenetics of a drug, the method comprising:

(a) providing a nucleic acid sample from a human;

(b) determining the presence of a OATP-C variant described herein; and (c) correlating (i) the identity of the nucleotide with (ii) the human's response following administration of a drug, thereby assessing the pharmacogenetics of the drug.

According to another aspect of the invention there is provided a computer-accessible medium comprising a database that includes a plurality of records, wherein each record associates (a) information that identifies a subject, with (b) information that indicates whether the subject has a variant described herein, and wherein each record further associates (a) with (c) information that identifies the presence or absence of an adverse event in the subject resulting from administration of an OATP-C-transportable drug to the subject.

According to another aspect of the invention there is provided an article of computer-readable medium having instructions encoded thereon, the instructions causing a processor to effect a method comprising:

(a) receiving information that indicates whether a subject has a variant described herein; and (b) suggesting an appropriate dosage of an OATP-C-transportable agent, wherein the suggestion is based on the information of (a).

Preferably the article is one wherein the suggested dosage is displayed in print or in an electronic format.

The invention will now be illustrated by the following non-limiting Examples in which.

FIG. 1 shows the effect of the V174A polymorphism on plasma levels of rosuvastatin. Correlation between genotype, for 3 non-synonymous SNPs in OATP-C, and dose-normalised plasma rosuvastatin values (ng/ml/mg) illustrates that the 174Ala variant is associated with higher plasma concentrations. (WT=wild-type homozygote, HET=heterozygote, VAR=homozygous variant.) None of the 52 subjects analysed were homozygous variant for either the Val174Ala or the Pro155Thr variants. Of the 52 subjects analysed, 42 were recorded as being of Caucasian origin. The other 10 subjects were either Hispanic, Black or Asian.

FIG. 2 shows the effect of the OATP-C*15 haplotype on plasma levels of rosuvastatin. Correlation between OATP-C haplotypes and dose-normalised plasma rosuvastatin values (ng/ml/mg) illustrates that the OATP-C*15 haplotype is associated with higher plasma concentrations. See Table 1 below for a description of amino acid variants for each haplotype. Results for subjects haplotype pairs with n=3 or fewer (*15/*14, *1b/*14, *1b/*15) are not shown.

In FIGS. 1 and 2, the lower and upper lines of the "box" are the 25th and 75th percentiles of the sample. The distance between the top and bottom of the box is the interquartile range. The line in the middle of the box is the sample median. The "whiskers", extending above and below the box, show the extent of the rest of the sample (unless there are outliers). Assuming no outliers, the maximum of the sample is the top of the upper whisker. The minimum of the sample is the bottom of the lower whisker. By default, an outlier is a value that is more than 1.5 times the interquartile range away from the top or bottom of the box. Individual data points are outliers.

FIG. 3 shows the effect of the Val174Ala variant on plasma levels of rosuvastatin in patients treated for 6 weeks with different doses of rosuvastatin. Plasma rosuvastatin levels at 6 weeks have been dose normalised for the analysis. Mean plasma rosuvastatin levels were higher in subjects heterozygous for the Val174Ala polymorphism, as compared to homozygous wild-type subjects (Val/Val). The association between the V174A variant allele and plasma rosuvastatin PK levels was most evident at the higher doses of rosuvastatin.

FIG. 4 shows that there is a trend for an increase in the mean plasma rosuvastatin concentrations in those subjects who are heterozygous for the SNP az0005537. This SNP is located within a putative NF1 transcription factor binding site at −118 bp upstream of the start of transcription. Data shown is for two independent phase III studies where PK data was collected. Genotype 1 1 is the wild-type homozygous genotype (az0005537 A/A) and genotype 1 2 is the heterozygous genotype (az0005537 A/C).

FIG. 5 shows that subjects that have the linked 174A variant and minor C allele at the az0005537 SNP have a tendency for higher mean plasma rosuvastatin concentrations in comparison to subjects with the V174 variant and the major common az0005537 allele (A). Hence the variant az0005537 allele (C) appears to have an additive effect on plasma rosuvastatin levels.

Since alleles of SNP az0005537 are in linkage disequilibrium with those of OATPC V174A, the variant allele at the SNP in the promoter region may increase the expression of the reduced function OATPC allele resulting in increased plasma rosuvastatin levels in subjects which have both of these polymorphic variants. Data shown is combined from 2 phase III clinical studies where PK data was collected. Subjects heterozygous for the V174A variant have been stratified into two groups based on the genotype for the promoter az0005537 polymorphism. NF1 WT=subjects with A/A wild-type genotype at the az0005537 SNP. NF1 het=subjects with the A/C heterozygous genotype at the AZ0005537 SNP.

EXAMPLE 1

Polymorphisms in OATP-C Affect the In Vivo Disposition of Statins in Patients

In brief, the OATP-C gene was sequenced in 79 human clinical trial subjects. 52 of these patients had received rosuvastatin for at least 6 weeks for dislipidaemic disease and had plasma PK measurements taken after 6 weeks of treatment. Data for these 52 patients were used to show that some polymorphic variants in OATP-C have a functionally significant effect on plasma levels of statins.

Methodology

The promoter, exons and 3' untranslated regions of OATP-C were fully sequenced by DNA terminator sequencing in DNA collected from 79 subjects in clinical trials. Sequencing traces were used to record the genotypes for known (i.e. available in the literature or SNP databases) SNPs in OATP-C. Some novel SNPs were found in the promoter and 3'UTR region of OATP-C.

Mean dose-normalised plasma rosuvastatin concentrations were determined for the genotypes for each polymorphic variant in the OATP-C gene. OATP-C genotype data for 3 SNPs, namely amino acid position 130 Asparagine→Aspartic acid (Asn130Asp), 155 Proline→Threonine (Pro 155Thr) and 174 Valine→Alanine (Val174Ala), was utilised to determine the haplotype pair for each subject. Mean dose-normalised plasma rosuvastatin concentrations were determined for the subjects grouped by haplotype pair.

All consenting subjects treated with rosuvastatin (n=271), from the 2 clinical trials including the original 52 patients, were subsequently genotyped, using TaqMan™, for OATP-C variants. Data for SNPs causing the N130D, P155T and V174A variants were utilised to assign OATPC haplotype pairs to each subject, as previously described.

Results

The sequencing data revealed a number of SNPs not previously reported, 8 in the promoter region (Jung, D. 2001 Journal of Biological Chemistry. 276(40), 37206-37214) and 4 in the 3'UTR region of OATP-C. These SNPs represent another aspect of the invention. These 12 novel SNPs were identified via sequencing the OATP-C gene in 79 subjects. Of these novel SNPs, 8 SNPs were located in the OATP-C promoter. 2 of these SNPs were located in consensus NF1 transcription factor binding sites at positions −26A>G and −118A>C relative to the transcription initiation site (see SEQ ID NO 2). Other novel upstream SNPs included, −309T>C, −878A>G, −903C>T, −1054G>T, −1215T>A and −1558 T>C, where nucleotide positions are relative to the transcription initiation site as described by Jung et al (SEQ ID NO 2). A further 4 novel SNPs were located in the 3'UTR region of the OATP-C gene, namely T2122G, C2158T, A2525C, and G2651A, where the nucleotide position is relative to the ATG (see SEQ ID NO 3).

OATP-C genotype data for 3 SNPs Asn130Asp, Pro 155Thr and Val174Ala was utilised to determine the haplotypes. The package SNPHAP (Clayton, David SNPHAPv0.2 2002 world wide web-gene at cimr.cam.ac.uk/clayton/software/snphap.txt) was used for this analysis. The haplotypes were also predicted using the PHASE package (Stephens, M. 2001 American Journal of Human Genetics 68, 978-989) and were found to give the same predicted haplotypes. The haplotypes were found to be concordant with those reported previously (Tirona 2001). The −118 A>C promoter SNP, at the NF1 binding site, was in strong linkage disequilibrium with the Val174Ala coding variant (delta=0.3).

TABLE 1

Common haplotypes in the OATP-C gene

| *nomenclature | Amino acid variant(s) on allele | Haplotype Frequency (n = 79) |
|---|---|---|
| *1a | Asn130, Pro155, Val174 | 57% |
| *1b | Asp130, Pro155, Val174 | 22% |
| *5 | Asn130, Pro155, Ala174 | 2% |
| *14 | Asp130, Thr155, Val174 | 7.5% |
| *15 | Asp130, Pro155, Ala174 | 11.5% |

TABLE 2

Frequency of the more common non-synonymous OATP-C SNPs (n = 79)

| Amino Acid | Major allele | Minor allele | SNP | Frequency |
|---|---|---|---|---|
| 130 | Asn130 | Asp130 | A388G | 0.41 |
| 155 | Pro155 | Thr155 | C463A | 0.08 |
| 174 | Val174 | Ala174 | T521C | 0.13 |

TABLE 3

Individuals haplotypes for OATP-C

| Haplotype Pair | AZ haplotype ID | No of ind (total = 79) | Frequency |
|---|---|---|---|
| *1a/*1a | A | 28 | 35% |
| *1b/*1b | B | 7 | 9% |
| *1a/*1b | C | 14 | 18% |
| *1a/*15 | D | 13 | 16% |
| *1a/*14 | E | 6 | 7% |
| *1b/*15 | F | 3 | 4% |
| *1b/*14 | G | 3 | 4% |

TABLE 3-continued

Individuals haplotypes for OATP-C

| Haplotype Pair | AZ haplotype ID | No of ind (total = 79) | Frequency |
|---|---|---|---|
| *1a/*5 | H | 2 | 3% |
| *15/*14 | I | 3 | 4% |

TABLE 4

| PK GROUP | Val/Val | Val/Ala | Total |
|---|---|---|---|
| HIGH | 17 | 10 | 27 |
| LOW | 22 | 3 | 25 |
| Total | 39 | 13 | 52 |

Table 4 shows the distribution of genotypes for the V174A variant between subjects classified into 'high' and 'low' PK groups based on the distribution of rosuvastatin plasma PK levels in 2 phase III trials. The high and low sub-groups represent those subjects with PK values in the $10^{th}$ and $90^{th}$ percentiles compared to the distribution of plasma PK values observed for the complete trial cohort. The Val/Ala heterozygote genotype is more common in those subjects with 'high' plasma PK levels, and more frequent than would be expected by chance based on the population allele frequency of the V174A variant [chi squared p=0.037 when n=52 (all subjects) and p=0.019 when n=42 (Caucasian subjects only)] and [exact test p=0.055 when n=52 (all subjects) and p=0.043 when n=42 (Caucasian subjects only)].

Sequence and genotype data from 79 subjects was used to determine the allele and haplotype frequencies. Plasma rosuvastatin concentrations were only available for 52 of these 79 subjects and hence there were only small numbers of subjects for some of the haplotype pair groups.

The V174A variant usually occurs as the OATPC*5 allele. The V174A variant has also been observed on the OATPC*5 allele in Caucasian populations, but not in Japanese populations. However, statistically significant differences in frequencies of these alleles between populations have not been observed.

TABLE 5

Sequences

A) Protein Sequences
Protein sequences determined by translation of cDNA with accession number AF205071
1) Sequence of OATPC protein OATPC*1a (N130 and V174) - SEQ ID NO 1

```
MDQNQHLNKT AEAQPSENKK TRYCNGLKMF LAALSLSFIA KTLGAIIMKS      50

SIIHIERRFE ISSSLVGFID GSFEIGNLLV IVFVSYFGSK LHRPKLIGIG     100

CFIMGIGGVL TALPHFFMGY YRYSKETNIN SSENSTSTLS TCLINQILSL     150

NRASPEIVGK GCLKESGSYM WIYVFMGNML RGIGETPIVP LGLSYIDDFA     200

KEGHSSLYLG ILNAIAMIGP IIGFTLGSLF SKMYVDIGYV DLSTIRITPT     250

DSRWVGAWWL NFLVSGLFSI ISSIPFFFLP QTPNKPQKER KASLSLHVLE     300

TNDEKDQTAN LTNQGKNITK NVTGFFQSFK SILTNPLYVM FVLLTLLQVS     350

SYIGAFTYVF KYVEQQYGQP SSKANILLGV ITIPIFASGM FLGGYIIKKF     400
```

TABLE 5-continued

| Sequences | |
|---|---|
| KLNTVGIAKF SCFTAVMSLS FYLLYFFILC ENKSVAGLTM TYDGNNPVTS | 450 |
| HRDVPLSYCN SDCNCDESQW EPVCGNNGIT YISPCLAGCK SSSGNKKPIV | 500 |
| FYNCSCLEVT GLQNRNYSAH LGECPRDDAC TRKFYFFVAI QVLNLFFSAL | 550 |
| GGTSHVMLIV KIVQPELKSL ALGFHSMVIR ALGGILAPIY FGALIDTTCI | 600 |
| KWSTNNCGTR GSCRTYNSTS FSRVYLGLSS MLRVSSLVLY IILIYAMKKK | 650 |
| YQEKDINASE NGSVMDEANL ESLNKNKHFV PSAGADSETH C. | 692 |

2) Sequence of OATPC protein OATPC*15 (D130 and A174) - SEQ ID NO: 4

| | |
|---|---|
| MDQNQHLNKT AEAQPSENKK TRYCNGLKMF LAALSLSFIA KTLGAIIMKS | 50 |
| SIIHIERRFE ISSSLVGFID GSFEIGNLLV IVFVSYFGSK LHRPKLIGIG | 100 |
| CFIMGIGGVL TALPHFFMGY YRYSKETNI<u>D</u> SSENSTSTLS TCLINQILSL | 150 |
| NRASPEIVGK GCLKESGSYM WIY<u>A</u>FMGNML RGIGETPIVP LGLSYIDDFA | 200 |
| KEGHSSLYLG ILNAIAMIGP IIGFTLGSLF SKMYVDIGYV DLSTIRITPT | 250 |
| DSRWVGAWWL NFLVSGLFSI ISSIPFFFLP QTPNKPQKER KASLSLHVLE | 300 |
| TNDEKDQTAN LTNQGKNITK NVTGFFQSFK SILTNPLYVM FVLLTLLQVS | 350 |
| SYIGAFTYVF KYVEQQYGQP SSKANILLGV ITIPIFASGM FLGGYIIKKF | 400 |
| KLNTVGIAKF SCFTAVMSLS FYLLYFFILC ENKSVAGLTM TYDGNNPVTS | 450 |
| HRDVPLSYCN SDCNCDESQW EPVCGNNGIT YISPCLAGCK SSSGNKKPIV | 500 |
| FYNCSCLEVT GLQNRNYSAH LGECPRDDAC TRKFYFFVAI QVLNLFFSAL | 550 |
| GGTSHVMLIV KIVQPELKSL ALGFHSMVIR ALGGILAPIY FGALIDTTCI | 600 |
| KWSTNNCGTR GSCRTYNSTS FSRVYLGLSS MLRVSSLVLY IILIYAMKKK | 650 |
| YQEKDINASE NGSVMDEANL ESLNKNKHFV PSAGADSETH C. | 692 |

3) Sequence of OATPC protein OATPC*5 (N130 and A174) - SEQ ID NO: 5

| | |
|---|---|
| MDQNQHLNKT AEAQPSENKK TRYCNGLKMF LAALSLSFIA KTLGAIIMKS | 50 |
| SIIHIERRFE ISSSLVGFID GSFEIGNLLV IVFVSYFGSK LHRPKLIGIG | 100 |
| CFIMGIGGVL TALPHFFMGY YRYSKETN<u>IN</u> SSENSTSTLS TCLINQILSL | 150 |
| NRASPEIVGK GCLKESGSYM WIY<u>A</u>FMGNML RGIGETPIVP LGLSYIDDFA | 200 |
| KEGHSSLYLG ILNAIAMIGP IIGFTLGSLF SKMYVDIGYV DLSTIRITPT | 250 |
| DSRWVGAWWL NFLVSGLFSI ISSIPFFFLP QTPNKPQKER KASLSLHVLE | 300 |
| TNDEKDQTAN LTNQGKNITK NVTGFFQSFK SILTNPLYVM FVLLTLLQVS | 350 |
| SYIGAFTYVF KYVEQQYGQP SSKANILLGV ITIPIFASGM FLGGYIIKKF | 400 |
| KLNTVGIAKF SCFTAVMSLS FYLLYFFILC ENKSVAGLTM TYDGNNPVTS | 450 |
| HRDVPLSYCN SDCNCDESQW EPVCGNNGIT YISPCLAGCK SSSGNKKPIV | 500 |
| FYNCSCLEVT GLQNRNYSAH LGECPRDDAC TRKFYFFVAI QVLNLFFSAL | 550 |
| GGTSHVMLIV KIVQPELKSL ALGFHSMVIR ALGGILAPIY FGALIDTTCI | 600 |
| KWSTNNCGTR GSCRTYNSTS FSRVYLGLSS MLRVSSLVLY IILIYAMKKK | 650 |
| YQEKDINASE NGSVMDEANL ESLNKNKHFV PSAGADSETH C. | 692 |

B) Sequence of OATPC cDNA (AF205071) for 3'UTR SNPs
Coding region is nucleotides 135 to 2210. Position of polymorphisms downstream from the ATG (upper case) are described where the A of the ATG is +1.
Polymorphisms T2122G, C2158T, A2525C, G2651A are underlined TABLE 5-continued

| Sequences | | | | |
|---|---|---|---|---|
| SEQ ID NO: 3 | | | | |
| cggacgcgtg | ggcggacgcg | tgggtcgccc | acgcgtccga | cttgttgcag | 50 |
| ttgctgtagg | attctaaatc | caggtgattg | tttcaaactg | agcatcaaca | 100 |
| acaaaaacat | ttgtatgata | tctatatttc | aatcATGgac | caaaatcaac | 150 |
| atttgaataa | aacagcagag | gcacaacctt | cagagaataa | gaaaacaaga | 200 |
| tactgcaatg | gattgaagat | gttcttggca | gctctgtcac | tcagctttat | 250 |
| tgctaagaca | ctaggtgcaa | ttattatgaa | aagttccatc | attcatatag | 300 |
| aacggagatt | tgagatatcc | tcttctcttg | ttggttttat | tgacggaagc | 350 |
| tttgaaattg | gaaatttgct | tgtgattgta | tttgtgagtt | actttggatc | 400 |
| caaactacat | agaccaaagt | taattggaat | cggttgtttc | attatgggaa | 450 |
| ttggaggtgt | tttgactgct | ttgccacatt | tcttcatggg | atattacagg | 500 |
| tattctaaag | aaactaatat | cgattcatca | gaaaattcaa | catcgacctt | 550 |
| atccacttgt | ttaattaatc | aaattttatc | actcaataga | gcatcacctg | 600 |
| agatagtggg | aaaaggttgt | ttaaaggaat | ctgggtcata | catgtggata | 650 |
| tatgtgttca | tgggtaatat | gcttcgtgga | ataggggaga | ctcccatagt | 700 |
| accattgggg | ctttcttaca | ttgatgattt | cgctaaagaa | ggacattctt | 750 |
| ctttgtattt | aggtatattg | aatgcaatag | caatgattgg | tccaatcatt | 800 |
| ggctttaccc | tgggatctct | gttttctaaa | atgtacgtgg | atattggata | 850 |
| tgtagatcta | agcactatca | ggataactcc | tactgattct | cgatgggttg | 900 |
| gagcttggtg | gcttaatttc | cttgtgtctg | gactattctc | cattatttct | 950 |
| tccataccat | tcttttctctt | gccccaaact | ccaataaaac | cacaaaaaga | 1000 |
| aagaaaagct | tcactgtctt | tgcatgtgct | ggaaacaaat | gatgaaaagg | 1050 |
| atcaaacagc | taatttgacc | aatcaaggaa | aaaatattac | caaaaatgtg | 1100 |
| actggttttt | tccagtcttt | taaaagcatc | cttactaatc | ccctgtatgt | 1150 |
| tatgtttgtg | cttttgacgt | tgttacaagt | aagcagctat | attggtgctt | 1200 |
| ttacttatgt | cttcaaatac | gtagagcaac | agtatggtca | gccttcatct | 1250 |
| aaggctaaca | tcttattggg | agtcataacc | atacctattt | ttgcaagtgg | 1300 |
| aatgttttta | ggaggatata | tcattaaaaa | attcaaactg | aacaccgttg | 1350 |
| gaattgccaa | attctcatgt | tttactgctg | tgatgtcatt | gtccttttac | 1400 |
| ctattatatt | ttttcatact | ctgtgaaaac | aaatcagttg | ccggactaac | 1450 |
| catgacctat | gatggaaata | atccagtgac | atctcataga | gatgtaccac | 1500 |
| tttcttattg | caactcagac | tgcaattgtg | atgaaagtca | atgggaacca | 1550 |
| gtctgtggaa | acaatggaat | aacttacatc | tcaccctgtc | tagcaggttg | 1600 |
| caaatcttca | gtggcaata | aaaagcctat | agtgttttac | aactgcagtt | 1650 |
| gtttggaagt | aactggtctc | cagaacagaa | attactcagc | ccatttgggt | 1700 |
| gaatgcccaa | gagatgatgc | ttgtacaagg | aaattttact | tttttgttgc | 1750 |
| aatacaagtc | ttgaatttat | ttttctctgc | acttggaggc | acctcacatg | 1800 |
| tcatgctgat | tgttaaaatt | gttcaacctg | aattgaaatc | acttgcactg | 1850 |
| ggtttccact | caatggttat | acgagcacta | ggaggaattc | tagctccaat | 1900 |

TABLE 5-continued

Sequences

```
atattttggg gctctgattg atacaacgtg tataaagtgg tccaccaaca    1950
actgtggcac acgtgggtca tgtaggacat ataattccac atcattttca    2000
agggtctact tgggcttgtc ttcaatgtta agagtctcat cacttgtttt    2050
atatattata ttaatttatg ccatgaagaa aaaatatcaa gagaaagata    2100
tcaatgcatc agaaaatgga agtgtcatgg atgaagcaaa cttagaatcc    2150
ttaaataaaa ataaacattt tgtcccttct gctggggcag atagtgaaac    2200
acattgttaa ggggagaaaa aaagccactt ctgcttctgt gtttccaaac    2250
agcattgcat tgattcagta agatgttatt tttgaggagt tcctggtcct    2300
ttcactaaga atttccacat cttttatggt ggaagtataa ataagcctat    2350
gaacttataa taaacaaac tgtaggtaga aaaaatgaga gtactcattg     2400
ttacattata gctacatatt tgtggttaag gttagactat atgatccata    2450
caaattaaag tgagagacat ggttactgtg taataaaaga aaaaatactt    2500
gttcaggtaa ttctaattct taataaaaca aatgagtatc atacaggtag    2550
aggttaaaaa ggaggagcta gattcatatc ctaagtaaag agaaatgcct    2600
agtgtctatt ttattaaaca aacaaacaca gagtttgaac tataatacta    2650
aggcctgaag tctagcttgg atatatgcta caataatatc tgttactcac    2700
ataaaattat atatttcaca gactttatca atgtataatt aacaattatc    2750
ttgtttaagt aaatttagaa tacatttaag tattgtggaa gaaataaaga    2800
cattccaata tttgcaaaaa aaaaaaaaaa                          2830
```

C) Sequence of OATPC promoter region from AC022335
-26A>G or -118A>C, and -309T>C, -878A>G, -903C>T, -1054G>T,
-1215T>A or -1558 T>C, where nucleotide positions are
relative to the transcription initiation site (as defined
by Jung et al) and as according to the following promoter
and 5' flanking sequence (from AC022335).
The start of transcription is annotated with an arrow.
SNPs are marked in upper case.
SEQ ID NO: 2

```
atctcagaga ttttatttgt attcatttaa tataaattaa ctgctctaaa    -1951
atttataata tgcaaatatc atacaattaa tctaattagg tgttgaatct    -1901
ataatgtgcc aggcattatg taaggcactt tacatacact aaatctttat    -1851
tccaaatata gacttcttac tttatagatg agtgcactga tgctcagaaa    -1801
tggtaaataa cctactgatg tttatactgc tggcaggtag cagagacata    -1751
tcggcattta agtctttcag acttcaaagg ccatgatatt tcatcagagc    -1701
tgtgatagcc gttcctgaaa aaaatatcag ctgattcttt aaatcaattt    -1651
ttgtcatcta actgatgcgt ggctgttagc ataatattga tcttgaaaga    -1601
tgttttgcaa catctttccc ctggtgtact cttgttttc caTgatccca     -1551
caaaatgagc agtctaatta tttacacaat taggaagaga aaaggggcac    -1501
agagaatgct ctttgacctc tgaaaatatt ggagaatttt acaactggca    -1451
cctttagctc aggattataa aggttgttag ttagtttgta ctgttttatc    -1401
ttcattgtat ataatatata tattagtctc caaacatgtt gatgtgtttt    -1351
caatgaaatg gatgtctgag gagaaaacca ttagcctgag aaaacccaaa    -1301
ctgtattccc attgtgaata aaaggaagtc cataaaaatg atggaaaatg    -1251
```

TABLE 5-continued

Sequences

```
ttctgcattc ctgttatgat atcaaaatct ggcagTacat gaaaattttt    -1201 caaagtgctt atttaacagg cataatcttt ggtctcctga gccagaatct    -1151 gctgggtatg ggactggatt gctattttga caactcgcca gtagattctt    -1101 actcagcaga gtatttggaa gccttactct aatattttgg ccttggTtct    -1051 acatttctca gttctgcaca gtcattcttc ccctctacac tactctttag    -1001 tttgtctcat gattccaata ctctcaataa ttaaccaaga atagaactaa     -951 tcaatcagat aactgtggca cagacatcaa atacattttg ctgcaacCat     -900 atcaacaaat gtcccatgaa tgAtaagggg taaccatatt ctcatatatg     -851 catcctcaca ttaccacata tatatatgtg catatgtgta tacaggtaaa     -800 agtgtgtata tatgtataca tgtatgtttg tgtgtatata catacatata     -751 tcttcacact tttctgaaat atatatattt atgtgagaga agggtctgta     -700 ctttatttca gaagagagct taatgtccaa ggtataattg agagtctaaa     -651 atgtttgagt tattgaatta attaaacttc atctctactc aagaaaactt     -600 ttaactgagt taagctcttc ctttctccac aagtcaagtc aataaaagga     -551 aactgtgata ttaataattc tttcctgttt tgatgtaaag aatctatcgc     -501 ataaagcagt cttaattttc atcattcaga aaaatggtct tgcagttaat     -451 tgggactctc ttattccagg tggtatctcc agtctccata cataccacgt     -401 tagaaccata cttatgtacc aagcaaagag ggtatatttt aatttttaaa     -351 tgccaatgta acctgtaggc atatttttta tttgtcttaa aTtatttcct     -301 atttggaagt tttaaatacc tggaataatt tattgtactc atattttaa      -251 agaaaaaaat cttatgccac caacttaatt gaataaacaa cgtaaaagcca    -201 ttcccaaaag taaggtttac ttgttaagat taacaaaaaa taatgtgaga     -151 attctgagaa atataatctt taaatattgg caActggagt gaactcttaa     -101 aactaactag gttttatatg tttgactaga gcaatgacat aataaggtgg      -51 ttaatcatca ctggacttgt tttcAaaaag ccaactactt taagaggaat       -1 aaagggtgga cttgttgcag ttgctgtagg attctaaatc caggtaagaa
```

Conclusions

Evidence of an in vivo genotype-phenotype relationship has been determined between OATP-C variants and the pharmacokinetic profile of statins, a common class of drugs used in the treatment of hypercholesterolaemia/dyslipidaemia. The observation of higher plasma concentrations of rosuvastatin in patients with the Ala174 OATP-C variant indicates that transport of rosuvastatin by the Ala174 variant is lower than that of the Val174 OATP-C variant. The Ala174 variant thus causes reduced uptake of statins in to the liver and consequent increased plasma levels. Plasma drug concentration is a factor in altering the benefit-risk ratio of statin therapy. OATP-C variants N130D and P155T do not appear to affect the pharmacokinetic disposition of rosuvastatin.

The genotype-phenotype correlation between OATP-C variants and in vivo plasma levels of statins may be utilised to optimise the statin dose, appropriate for each individual, via a diagnostic assay for the SNP or protein variant. Optimisation of the plasma level will be important in subjects that require high doses of statins for adequate lowering of cholesterol levels to the desired threshold.

Evidence that polymorphisms in OATP-C affect the in vivo disposition of statins indicates that OATP-C variants may affect the clinical response to statins and other clinically relevant drugs that are transported by OATP-C. Correlation of polymorphisms in OATP-C with end of treatment dose-normalised plasma rosuvastatin concentrations, determined in subjects treated for 6 weeks with different doses of rosuvastatin, have shown that OATP-C variants have a functional effect on the in vivo pharmacokinetic disposition of rosuvastatin. Subjects heterozygous for the Val174Ala variant have increased mean plasma concentrations of rosuvastatin as compared to subjects homozygous for the wild-type Val174 variant at amino acid position 174. Subjects with a single copy of the OATP-C*15 allele (heterozygous for the Val174Ala and Asn130Asp variants) were found to have higher mean plasma concentrations than subjects with the OATP-C*1a, OATP-C*1b, and OATP-C*14 haplotypes. The observation of higher concentrations of rosuvastatin in subjects with the Ala174 OATP-C variant indicates that transport by the Ala174 variant is lower than that of the Val174 OATP-C variant. The Ala174 variant causes reduced uptake of statins into the liver and has an impact on the clinical response to statins. OATP-C variants affecting the pharmacokinetic profile of statins may be associated with a decreased benefit-risk ratio of statin therapy as a result of the high concentrations of statins in the circulation. The genotype-phenotype correlation between OATP-C variants and in vivo plasma levels of statins may be utilised to optimise the statin dose, appropriate for each individual, via a diagnostic assay for the SNP or protein variant. Optimisation of the plasma level will be important in subjects that require high doses of statins for adequate lowering of cholesterol levels to the desired threshold.

EXAMPLE 2

Evidence for Functional Significance of NF1 SNP (az0005537)

Figure 1:
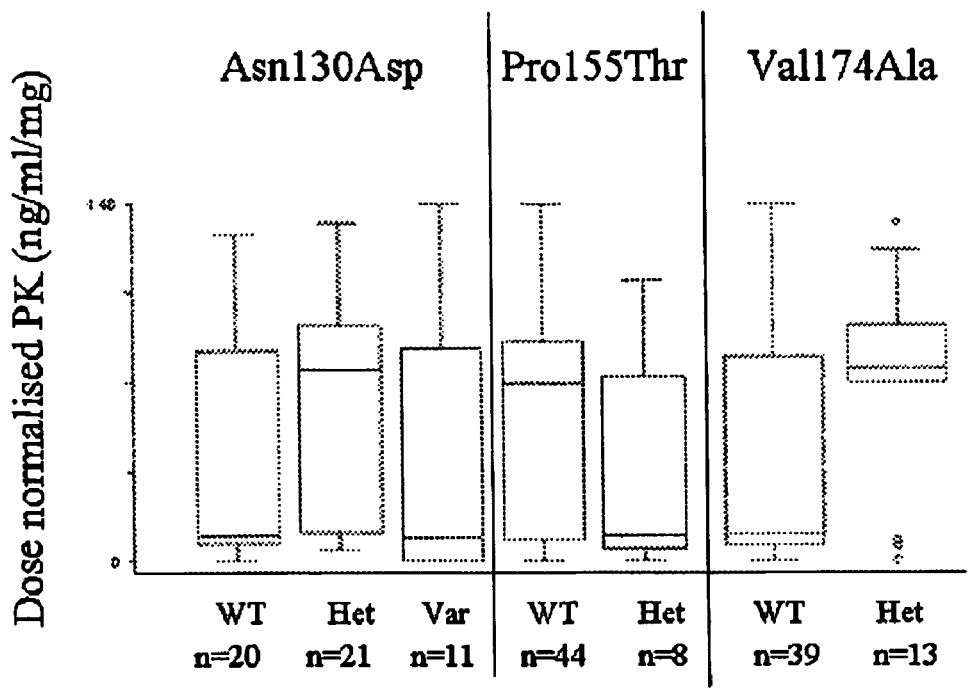
Figure 2:
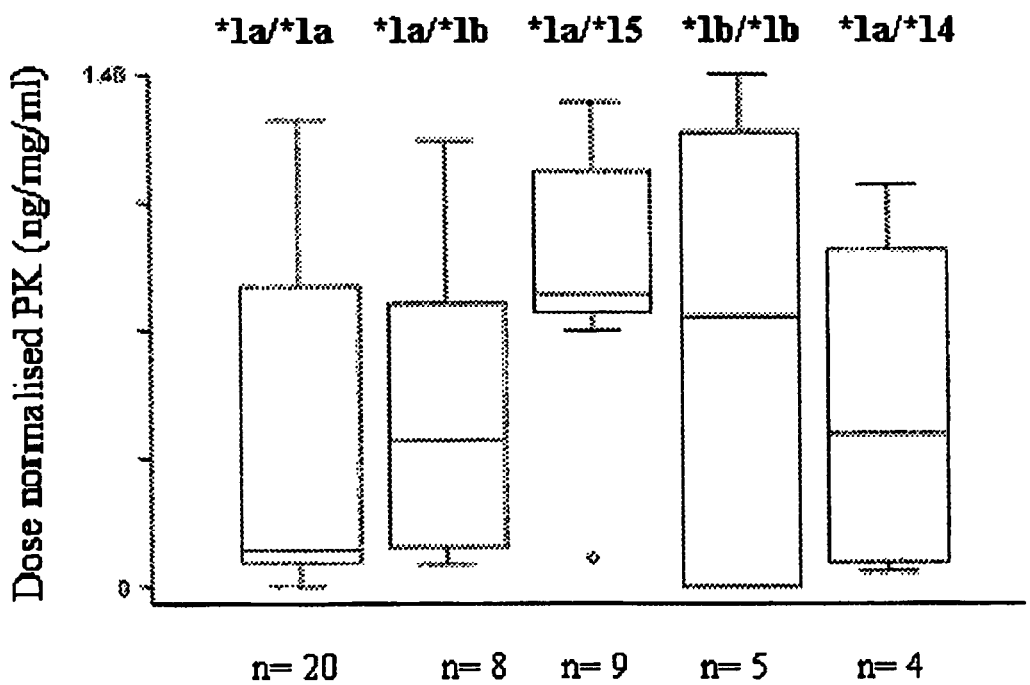
Figure 3:
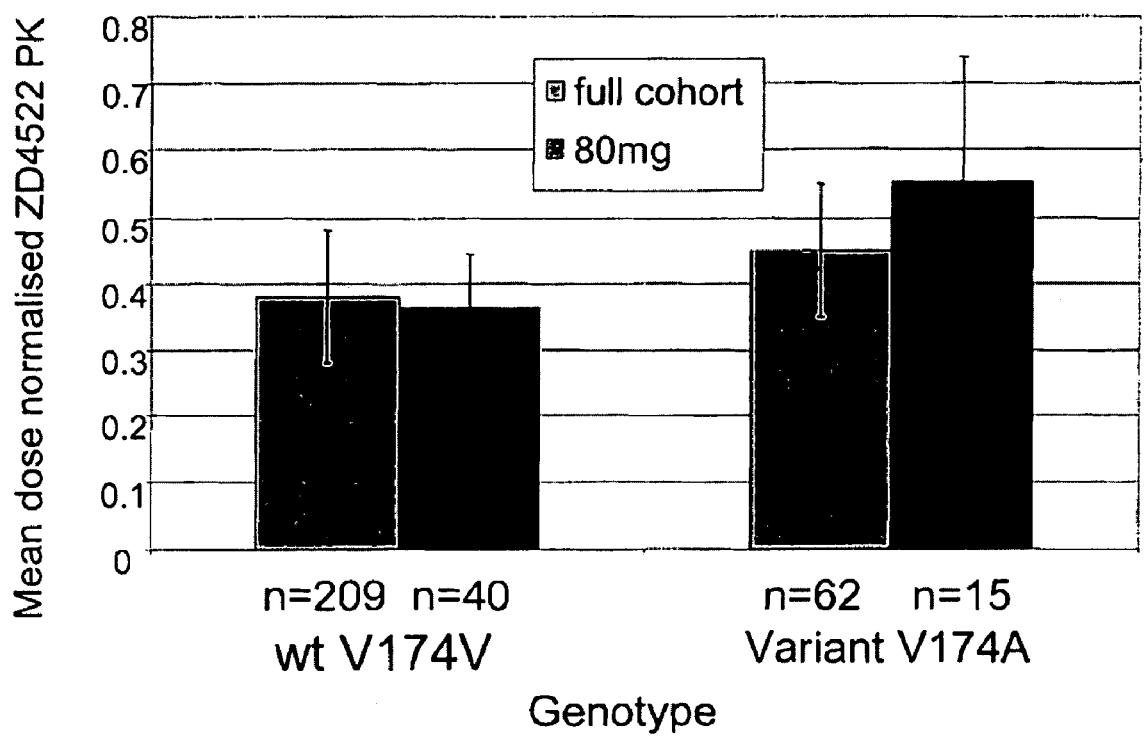
Figure 4:
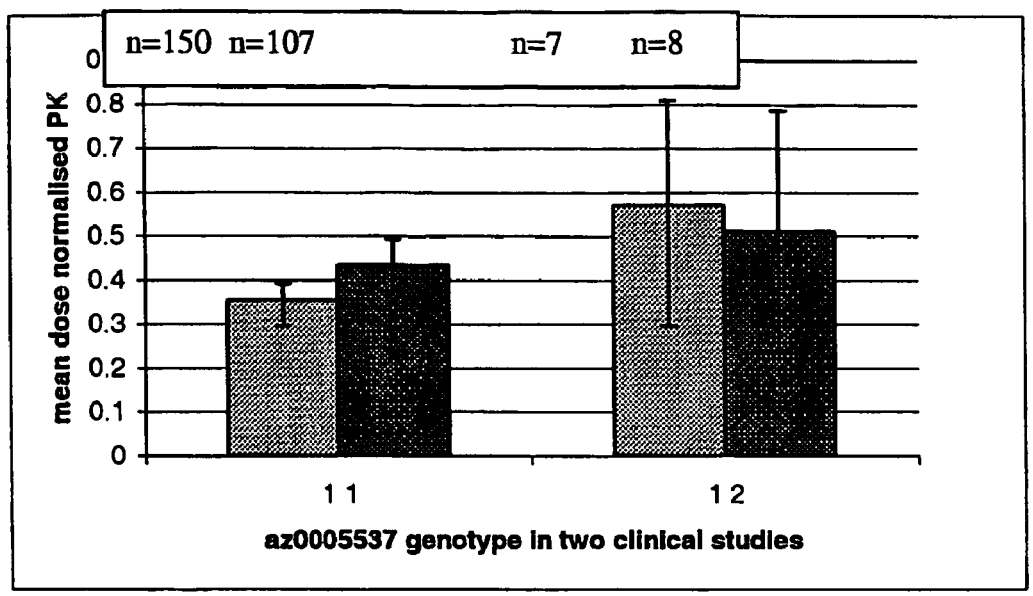
FIG. 4 shows that there is a trend for an increase in the mean plasma rosuvastatin concentrations in those subjects who are heterozygous for the SNP az0005537. This SNP is located within a putative NF1 transcription factor binding site at −118 bp upstream of the start of transcription.
Figure 5:
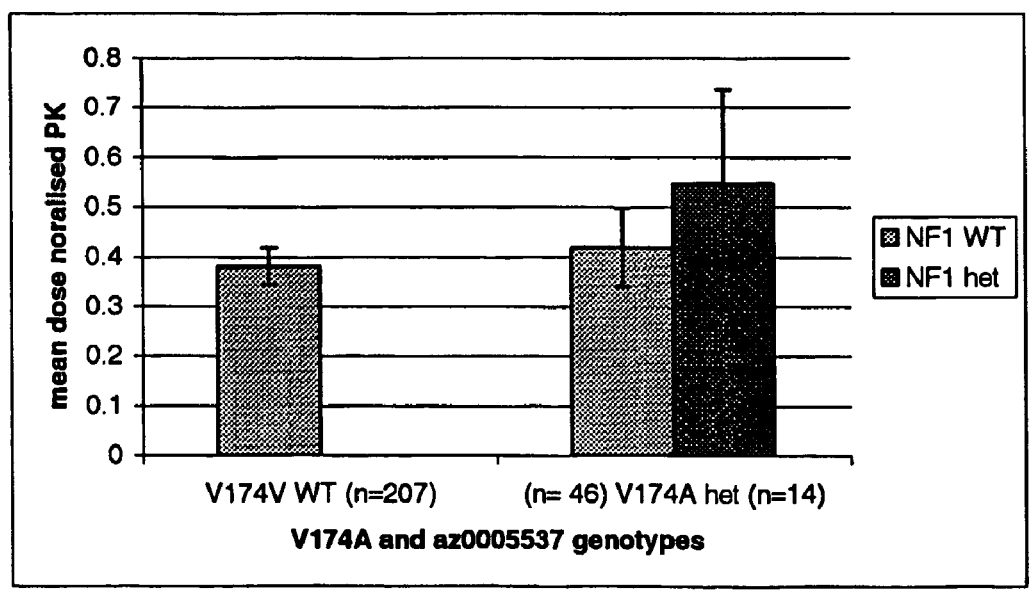
FIG. 5 shows that subjects that have the linked 174A variant and minor C allele at the az0005537 SNP have a tendency for higher mean plasma rosuvastatin concentrations in comparison to subjects with the V174 variant but the major common az0005537 allele (A). Hence the variant az0005537 allele (C) appears to have an additive effect on plasma rosuvastatin levels.

Since alleles of SNP az0005537 are in linkage disequilibrium with those of OATPC V174A, the variant allele at the SNP in the promoter region may increase the expression of the reduced function OATPC allele resulting in increased plasma rosuvastatin levels in subjects which have both of these polymorphic variants.

When considering V174A alone with the full cohort of samples (n=267), V174A WT compared to V174A heterozygote has a t-test value of $p=0.055$. However, if V174V WT vs V174A&NF1 (az0005537) compound heterozygote is considered, then the t-test value is $p=0.032$, which is statistically significant. This suggests that the OATPC NF1 SNP may also be a determinant of the pharmacokinetic disposition of rosuvastatin. Preliminary in vitro functional data supports the hypothesis that the variant C az0005537 allele is associated with increased expression. The promoter polymorphism may drive differential allelic expression with greater expression of the reduced function OATPC allele.

EXAMPLE 3

Linkage Disequilibrium

The polymorphism −118A>C or −1558T>C of SEQ ID NO:2 were analysed as set out below.

Alleles of polymorphisms at −118 and −1558 are in significant linkage disequilibrium with the alanine allele at position 174 of SEQ ID NO:1 ($p=0.009$ and $0.025$ respectively, analysed by the ASSOCIATE program, see Ott J (1999) Analysis of human genetic linkage, 3rd edition. Johns Hopkins University Press, Baltimore).

The invention claimed is:

1. A method of diagnosis comprising:
 (a) providing a biological sample from a human identified as being in need of treatment with rosuvastatin, wherein the sample comprises a nucleic acid encoding OATP-C;
 (b) testing the nucleic acid for the presence, on at least one allele, of
 a codon encoding alanine instead of valine at amino acid position 174 of SEQ ID NO:1; and
 (c) if the codon encoding alanine is found in at least one allele, diagnosing the human as likely to have reduced ability to transport rosuvastatin into liver cells.

2. A method according to claim 1, further comprising testing the nucleic acid for the presence, on at least one allele, of either or both of a −118A>C and a −1558T>C polymorphism of SEQ ID NO:2.

3. A method according to claim 1, wherein the human is being treated with one dose level of rosuvastatin and step (c) further comprises diagnosing the human as suitable for titration to another higher, rosuvastatin dose level if at least one allele encodes alanine instead of valine at amino acid position 174 of SEQ ID NO:1.

4. A method according to claim 1 wherein the human is being treated with at least 5 mg of rosuvastatin daily.

5. A method according to claim 1 wherein the human is being treated with at least 10 mg of rosuvastatin daily.

6. A method according to claim 1 wherein the human is being treated with at least 20 mg of rosuvastatin daily.

7. A method according to claim 1 wherein the human is being treated with at least 40 mg of rosuvastatin daily.

8. A method of diagnosis comprising:
 (a) providing a biological sample from a human identified as being in need of treatment with rosuvastatin, wherein the sample comprises an OATP-C polypeptide;
 (b) determining whether the OATP-C polypeptide comprises an alanine instead of a valine at position 174 of SEQ ID NO:1; and
 (c) if the amino acid at position 174 of SEQ ID NO:1 is an alanine, diagnosing the human as likely to have a reduced ability to transport rosuvastatin into liver cells.

9. A method according to claim 8, wherein the human is being treated with one dose level of rosuvastatin and step (c) further comprises diagnosing the human as suitable for titration to another, higher rosuvastatin dose level if the amino acid is an alanine.

10. A method according to claim 8, the method further comprising measuring the level of OATP-C polypeptide expression.

11. A method according to claim 8, the method further comprising determining, in a sample of nucleic acid from the human, the presence or absence, on at least one allele, of a cytosine at position −118 of SEQ ID NO:2, wherein the presence of the cytosine, combined with the determination that the OATP-C polypeptide of (b) comprises an alanine instead of a valine at position 174 of SEQ ID NO:1, is a further indication that the human is likely to have reduced ability to transport rosuvastatin into liver cells.

12. A method according to claim 8, wherein the human is being treated with at least 5 mg of rosuvastatin daily.

13. A method according to claim 8, wherein the human is being treated with at least 10 mg of rosuvastatin daily.

14. A method according to claim 8, wherein the human is being treated with at least 20 mg of rosuvastatin daily.

15. A method according to claim 8, wherein the human is being treated with at least 40 mg of rosuvastatin daily.

16. A method according to claim 1, wherein the nucleic acid is further tested for the presence, on at least one allele, of a cytosine at position −118 of SEQ ID NO:2.

* * * * *